United States Patent [19]
Leplatois et al.

[11] Patent Number: 5,407,822
[45] Date of Patent: Apr. 18, 1995

[54] ARTIFICIAL PROMOTER FOR THE EXPRESSION OF PROTEINS IN YEAST

[75] Inventors: Pascal Leplatois, Cuq Toulza; Gérard Loison, Toulouse; Bernard Pessegue, Muret; David Shire, Ramonville St Agne, all of France

[73] Assignee: Sanofi, Paris, France

[21] Appl. No.: 86,410

[22] Filed: Jul. 6, 1993

Related U.S. Application Data

[63] Continuation of Ser. No. 768,083, Oct. 2, 1991, abandoned.

[51] Int. Cl.$^6$ .......................... C12N 1/16; C12N 1/19; C12N 15/81; C12N 15/11
[52] U.S. Cl. .................... 435/254.21; 435/254.2; 435/320.1; 536/24.1
[58] Field of Search ............... 536/24.1; 435/69.1, 435/254.21, 320.1, 254.2

[56] References Cited

U.S. PATENT DOCUMENTS 3,810,820  5/1974  Laboureur et al. ............... 435/191

FOREIGN PATENT DOCUMENTS 164556  12/1985  European Pat. Off. .
174585  3/1986   European Pat. Off. .
273800  7/1988   European Pat. Off. .
284044  9/1988   European Pat. Off. .

OTHER PUBLICATIONS

Y. Lorch et al. "A region Flanking the GAL7 Gene and a Binding Site for GAL4 Protein as Upstream Activating Sequences in Yeast", J. Mol. Biol. vol. 186, 1985, pp. 821–824.

Tajima et al. "Duplicate Upstream Activating Sequences in the Promoter Region of the Saccharomyces Cerevisiae GAL7 Gene", Molecular and Cellular Biology, vol. 6, No. 1, Jan. 1986, pp. 246–256.

Russell et al. "Nucleotide Sequence of the Yeast Alcohol Dehydrogenase II Gene", J. Biol. Chem., vol. 258, No. 4, Feb. 1983, pp. 2674–2682.

Kingsman et al., "Heterologous Gene Expression in Saccharomyces cerevisiae," Biotechnology and Genetic Engineering Reviews 3:377–416. (Sep. 1985).

Derwent Abstract of Japan 1–51089 (Feb. 27, 1989).

Leplatois et al. (1992), Gene 122:139–145.

Singh et al., Nucl Acids Res., vol. 11, 1983, pp. 4049–4063.

Primary Examiner—Richard A. Schwartz
Assistant Examiner—Philip W. Carter
Attorney, Agent, or Firm—Foley & Lardner

[57] ABSTRACT

The invention relates to an artificial promoter for the expression of proteins, especially urate oxidase in yeast, which comprises:
- a sub-sequence upstream from the TATA component of the sequence of the promoter of the GAL7 gene of Saccharomyces cerevisiae, which comprises the upstream activation sequences UAS1 and UAS2; and
- a sub-sequence of the sequence of an ADH$_2$ promoter comprising the TATA component and the transcription initiation region.

8 Claims, 13 Drawing Sheets

FIG. 3A

```
  1  AAACCCTCACTGCCTCTCTCATTCCTTCCG  GTGCCCCCGATCCCTCAATCCAACTTGTACA   60
 61  TACTTCTCCCAACTCTCTGCTATATCCTTC  ATATTCCCATACTACAAGATGTCCGCAGTA   120
121  AAAGCAGCCCGCTACGGCAAGGACAATGTC  CGCGTCTACAAGGTTCACAAGGACGAGAAG   180
181  ACCGGTGTCCAGACGGTGTACGAGATGACC  GTCTGTGTGCTTCTGGAGGGTGAGATTGAG   240
241  ACCTCTTACACCAAGGCCGACAACAGCGTC  ATTGTCGCAACCGACTCCATTAAGAACACC   300
        ↓
301  ATTTACATCACCGCCAAGCAGAACCCCGTT  ACTCCTCCCGAGCTGTTCGGCTCCATCCTG   360
361  GGCACACACTTCATTGAGAAGTACAACCAC  ATCCATGCCGCTCACGTCAACATTGTCTGC   420
421  CACCGCTGGACCCGGATGGACATTGACGGC  AAGCCACACCCTCACTCCTTCATCCGCGAC   480
                                   A*
481  AGCGAGGAGAAGCGGGAATGTGCAGGTGGAC GTGGTCGAGGGCAAGGCATCGATATCAAG    540
541  TCGTCTCTGTCCGGCCTGACCGTGCTGAAG  AGCACCAACTCGCAGTTCTGGGGCTTCCTG   600
```

```
     FROM FIG. 3A                              FROM FIG. 3A
601  CGTGACGAGTACACCACACTTAAGGAGACC  TGGGACCGTATCCTGAGCACCGACGTCGAT   660
661  GCCACTTGGCAGTGGAAGAATTTCAGTGGA  CTCCAGGAGGTCCGCTCGCACGTGCCTAAG   720
721  TTCGATGCTACCCTGGGCCACTGCTCGCGAG GTCACTCTGAAGACTTTGCTGAAGATAAC    780
781  AGTGCCAGCGTGCAGGCCACTATGTACAAG  ATGGCAGAGAGCAAATCCTGGGCGCCAGCAG  840
841  CTGATCGAGACTGTCGAGTACTCGTTGCCT  AACAAGCACTATTTCGAAATCGACCTGAGC   900
     G*
901  TGGCACAAGGGCCTCCAAAACACCGGCAAG  AACGCCGAGGTCTTCGCTCCTCAGTCGGAC   960
961  CCCAACGGTCTGATCAAGTGTACCGTCGGC  CGGTCCTCTCTGAAGTCTAAATTGTAAACC   1020
1021 AACATGATTCTCACGTTCCGGAGTTTCCAA  GGCAAACTGTATATAGTCTGGGATAGGGTA   1080
1081 TAGCATTCATTCACTTGTTTTTTACTTCCA  AAAAAAAAAA                       1121
```

FIG. 4A

```
109 ATGTCCGCAGTAAAAGCAGCCCGCTACGGC AAGGACAATGTCCGCGTCTACAAGGTTCAC 168
  1 MetSerAlaValLysAlaAlaArgTyrGly LysAspAsnValArgValTyrLysValHis  20

169 AAGGACGAGAAGACCGGTGTCCAGACGGTG TACGAGATGACCGTCTGTGTGCTTCTGGAG 228
 21 LysAspGluLysThrGlyValGlnThrVal TyrGluMetThrValCysValLeuLeuGlu  40

229 GGTGAGATTGAGACCTTCTACACCAAGGCC GACAACAGCGTCATTGTCGCAACCGACTCC 288
 41 GlyGluIleGluThrSerTyrThrLysAla AspAsnSerValIleValAlaThrAspSer  60
                                  ──────V3─────

289 ATTAAGAACACCATTACATCACCGCCAAG CAGAACCCCGTTACTCCTCCCGAGCTGTTC  348
 61 IleLysAsnThrIleTyrIleThrAlaLys GlnAsnProValThrProProGluLeuPhe  80
                                           ─────T32/T33──────

349 GGCTCCATCCTGGGCACACACTTCATTGAG AAGTACAACCACATCCATGCCGCTCACGTC 408
 81 GlySerIleLeuGlyThrHisPheIleGlu LysTyrAsnHisIleHisAlaAlaHisVal 100

409 AACATTGTCTGCCACCGCTGGACCCGGATG GACATTGACGGCAAGCCACACCCTCACTCC 468
101 AsnIleValCysHisArgTrpThrArgMet AspIleAspGlyLysProHisProHisSer 120

469 TTCATCCGCGACAGGGAGGAGAAGGGAAT GTGCAGGTGGACGTGGTCGAGGGCAAGGGC  528
121 PheIleArgAspSerGluGluLysArgAsn ValGlnValAspValValGluGlyLysGly 140
                                                    ─────T17────→↑↓

529 ATCGATATCAAGTCGTCTCTGTCCGGCCTG ACCGTGCTGAAGAGCACCAACTCGCAGTTC 588
141 IleAspIleLysSerSerLeuSerGlyLeu ThrValLeuLysSerThrAsnSerGlnPhe 160
                ──V5/V6─                                     ──T31

589 TGGGGCTTCCTGCGTGACGAGTACACCACA CTTAAGGAGACCTGGGACCGTATCCTGAGC 648
161 TrpGlyPheLeuArgAspGluTyrThrThr LeuLysGluThrTrpAspArgIleLeuSer 180

649 ACCGACGTCGATGCCACTTGGCAGTGGAAG AATTTCAGTGGACTCCAGGAGGTCCGCTCG 708
181 ThrAspValAspAlaThrTrpGlnTrpLys AsnPheSerGlyLeuGlnGluValArgSer 200
        ──────T28──────                         ─────T20─────
```

```
↑ FROM FIG. 4A                                                                          FROM FIG. 4A ↑

709  CACGTGCCTAAGTTCGATGCTACCTGGGCC   ACTGCTCGCGAGGTCACTCTGAAGACTTT  768
201  HisValProLysPheAspAlaThrTrpAla   ThrAlaArgGluValThrLeuLysThrPhe 220
                          T23

769  GCTGAAGATAACAGTGCCAGCGTGCAGGCC   ACTATGTACAAGATGGCAGAGCAAATCCTG  828
221  AlaGluAspAsnSerAlaSerValGlnAla   ThrMetTyrLysMetAlaGluGlnIleLeu 240
                          V2

829  GCGCGCCAGCAGCTGATCGAGACTGTCGAG   TACTCGTTGCCTAACAAGCACTATTTCGAA  888
241  AlaArgGlnGlnLeuIleGluThrValGlu   TyrSerLeuProAsnLysHisTyrPheGlu 260
                                                              T29/

889  ATCGACCTGAGCTGGCACAAGGGCCTCCAA   AACACCGGCAAGAACGCCGAGGTCTTCGCT  948
261  IleAspLeuSerTrpHisLysGlyLeuGln   AsnThrGlyLysAsnAlaGluValPheAla 280
           T27                                     V1

949  CCTCAGTCGGACCCCAACGGTCTGATCAAG   TGTACCGTCGGCCGGTCCTCTCTGAAGTCT 1008
281  ProGlnSerAspProAsnGlyLeuIleLys   CysThrValGlyArgSerSerLeuLysSer 300

1009 AAATTGTAA
301  LysLeuEnd
```

ARTIFICIAL PROMOTER FOR THE EXPRESSION OF PROTEINS IN YEAST

This application is a continuation of application Ser. No. 07/768,083, filed Oct. 2, 1991, now abandoned.

The present invention relates to a novel artificial promoter for the expression of proteins, in particular heterologous proteins, in yeast, to a vector for the expression of said proteins which carries said promoter, to the strains of yeast, and especially of *Saccharomyces cerevisiae*, which are transformed by this expression vector, and to a method of producing a recombinant protein with the aid of these strains.

Yeast, and in particular *Saccharomyces cerevisiae*, a non-pathogenic microorganism whose genetics has been studied in detail, is a preferred eukaryotic host for the expression of proteins, especially heterologous proteins. It is therefore important to discover or construct novel promoters for the expression of said proteins which are more advantageous than the known promoters.

The structure of a yeast promoter, which is a DNA sequence located upstream from a gene and responsible for the transcription of said gene, is beginning to be partially known and understood. Said promoter is known to comprise a TATA component located in an AT-rich zone, a transcription initiation region downstream from said component and, if appropriate, upstream from said component, sequences, called upstream activation sequences (UAS) or upstream repression sequences (URS), which regulate the strength of the promoter under the effect of an inducer or a repressor.

The Applicant constructed a novel hybrid promoter from two known promoters: the promoter of the GAL7 gene of *Saccharomyces cerevisiae* (TAJIMA et al., 1986, Molecular Cellular Biology, 6, 246–256) and a promoter with a sequence similar to that of the natural ADH$_2$ promoter (5'-flanking region of the ADH$_2$ gene, described by RUSSEL et al. (1983), J. Biol. Chem. 258, 2674–2682), which is called an ADH$_2$ promoter in the present patent application.

The invention therefore relates to a novel artificial promoter for the expression of proteins in yeast, which comprises:

a sub-sequence upstream from the TATA component of the sequence of the promoter of the GAL7 gene of *Saccharomyces cerevisiae*, which comprises the upstream activation sequences UAS1 and UAS2; and a sub-sequence of the sequence of an ADH$_2$ promoter comprising the TATA component and the transcription initiation region.

Preferably, the sub-sequence upstream from the TATA component of the promoter of the GAL7 gene of *Saccharomyces cerevisiae* is the following sequence or a sub-sequence thereof (SEQ ID NO: 1):

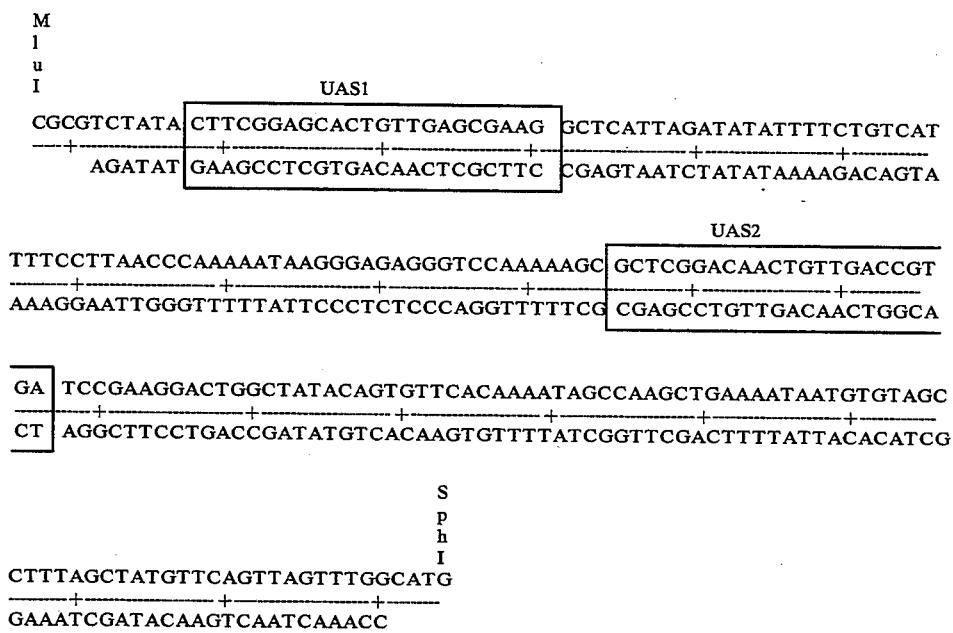

The sub-sequence of the sequence of an ADH$_2$ promoter comprising the TATA component and the transcription initiation region is preferably selected from the following sequence or a sub-sequence thereof (SEQ ID NO: 3):

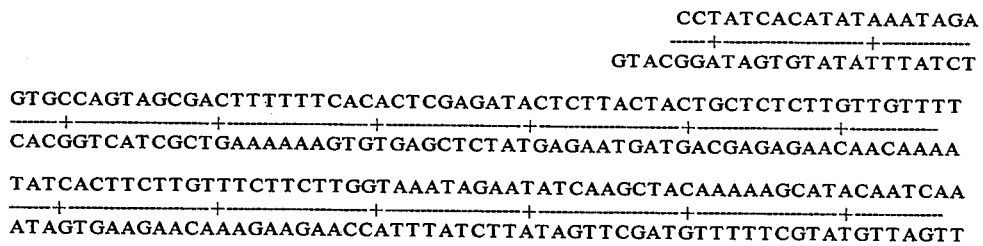

```
                    C
                    l
                    a
                    I
CTATCAACTATTAACTATAT|
----+---------------+--------   \
GATAGTTGATAATTGATATAGC
```

A Particularly advantageous promoter is that which comprises the following sequence (SEQ ID NO: 3):

```
        M
        l
        u
        I
CGCGTCTATACTTCGGAGCACTGTTGAGCGAAGGCTCATTAGATATATTTTCTGTCAT
----+---------------+---------------+---------------+--------
    AGATATGAAGCCTCGTGACAACTCGCTTCCGAGTAATCTATATAAAAGACAGTA

TTTCCTTAACCCAAAAATAAGGGAGAGGGTCCAAAAAGCGCTCGGACAACTGTTGACCGT
----+---------------+---------------+---------------+---------------+--------
    AAAGGAATTGGGTTTTTATTCCCTCTCCCAGGTTTTTCGCGAGCCTGTTGACAACTGGCA

GATCCGAAGGACTGGCTATACAGTGTTCACAAAATAGCCAAGCTGAAAATAATGTGTAGC
----+---------------+---------------+---------------+---------------+--------
    CTAGGCTTCCTGACCGATATGTCACAAGTGTTTTATCGGTTCGACTTTTATTACACATCG

S
                               p
                               h
                               I
CTTTAGCTATGTTCAGTTAGTTTGGCATGCCTATCACATATAAATAGA
----+---------------+---------------+---------------+-------
    GAAATCGATACAAGTCAATCAAACCGTACGGATAGTGTATATTTATCT

GTGCCAGTAGCGACTTTTTTCACACTCGAGATACTCTTACTACTGCTCTCTTGTTGTTTT
----+---------------+---------------+---------------+---------------+--------
    CACGGTCATCGCTGAAAAAAGTGTGAGCTCTATGAGAATGATGACGAGAGAACAACAAAA

TATCACTTCTTGTTTCTTCTTGGTAAATAGAATATCAAGCTACAAAAAGCATACAATCAA
----+---------------+---------------+---------------+---------------+--------
    ATAGTGAAGAACAAAGAAGAACCATTTATCTTATAGTTCGATGTTTTCGTATGTTAGTT

C
                    l
                    a
                    I
CTATCAACTATTAACTATAT|
----+---------------+--------   \
GATAGTTGATAATTGATATAGC
```

The promoter of the invention may be obtained by the conventional recombinant DNA techniques well-known to anyone skilled in the art, The promoter of the invention has important advantages over the known promoters and in particular over the ADH$_2$ promoter and the promoter of the GAL7 gene.

It permits a high maximum level of transcription and hence of expression, in particular for *A. flavus* urate oxidase, and offers the possibility of regulating said expression at three levels:

zero level in the presence of glucose and in the absence of galactose: no expression is detected, which is an identical result to that published for the promoter of the GAL7 gene in a strain of *Saccharomyces cerevisiae* growing under these conditions (TAJIMA et al., 1986, Molecular Cellular Biology, 6, 246–256). The ADH$_2$ promoter shows a low but detectable level of expression under these conditions.

basic level in the absence of glucose and galactose: there is weak expression, which is an intermediate result between that observed for the ADH$_2$ promoter (maximum level) and that published for the promoter of the GAL7 gene (zero level: TAJIMA et al., 1986, Molecular Cellular Biology, 6, 246–256).

maximum level of expression in the absence of glucose and in the presence of galactose.

The advantage, for the expression of heterologous proteins in yeast, of having a promoter which shows a zero level under certain conditions is that it affords the possibility of avoiding any selection pressure which would favor the least productive cells during the propagation of the strain. This is particularly important in the case where the protein is toxic to the host cell.

The advantage of a promoter with two levels of expression: the one a basic level (non-induced) and the other a maximum level (induced), lies in the ability to choose an intermediate level by varying the concentration of the inducer.

The invention further relates to an expression vector for yeast which carries a gene of interest with the means necessary for its expression, its replication and the selection of the transformed cells, wherein the gene of interest is under the control of the promoter defined above.

This gene of interest can be an endogenous gene of yeast or a eukaryotic or prokaryotic exogenous gene.

Of particular value as eukaryotic exogenous genes are a recombinant gene coding for *Aspergillus flavus* urate oxidase, a recombinant gene coding for a human cytokinin and a recombinant gene coding for hirudin.

In the case where the protein coded for by the exogenous gene is secreted naturally, the sequence coding for this protein is preferably preceded by a signal sequence. The function of this signal sequence, which is chosen according to the host cell, is to permit export of the recombinant protein out of the cytoplasm, enabling the recombinant protein to adopt a configuration similar to that of the natural protein and considerably facilitating its purification. This signal sequence can be cleaved either in a single step by a signal peptidase which releases the mature protein, the eliminated sequence usually being called a pre sequence or signal peptide, or in several steps when this signal sequence comprises, in addition to the sequence eliminated by the signal peptidase, called a pre sequence, a sequence eliminated later in the course of one or more proteolytic events, called a pro sequence.

The invention further relates to the strains of yeast, in particular of *Saccharomyces cerevisiae*, which are transformed by the above expression vector, and to a method of producing a protein of interest, which comprises the culture of said strains in the presence of galactose.

In particular, the invention relates to the strains of *Saccharomyces cerevisiae* which have been deposited in the depository authority named Collection Nationale de Culture de Microorganismes—Intitut Pasteur—France under the following numbers:

I-919 on Dec. 28, 1989
I-1021 on December, 1990
I-1022 on December, 1990
I-1023 on December, 1990

BRIEF DESCRIPTION OF THE DRAWINGS

FIGS. 3A and 3B show the nucleotide sequence (SEQ ID NO: 36) of clone 9C and a portion of clone 9A; the arrow indicates the start of clone 9A.

FIGS. 4A and 4B show the DNA and amino sequence (SEQ ID NO: 37) starting with the ATG codon at position 109 in FIG. 3 and the corresponding coded polypeptide. The sequenced peptides obtained by hydrolysis of the urate oxydase of *A. flavus* using trypsin and protease V8 are represented by arrows indicating the coded peptides, as follows:

solid arrow = tryptic peptide
dashed arrow = peptide obtained by protease V8 hydrolysis.

Figure 5:
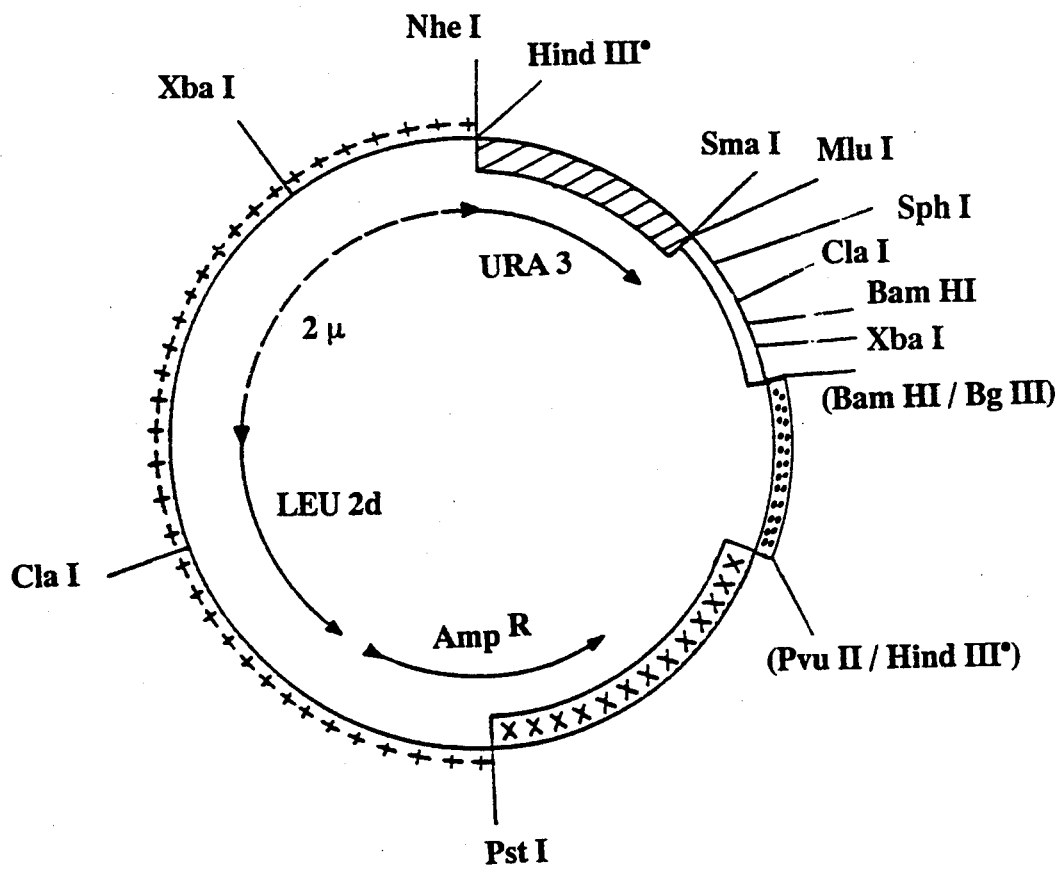
Figure 6:
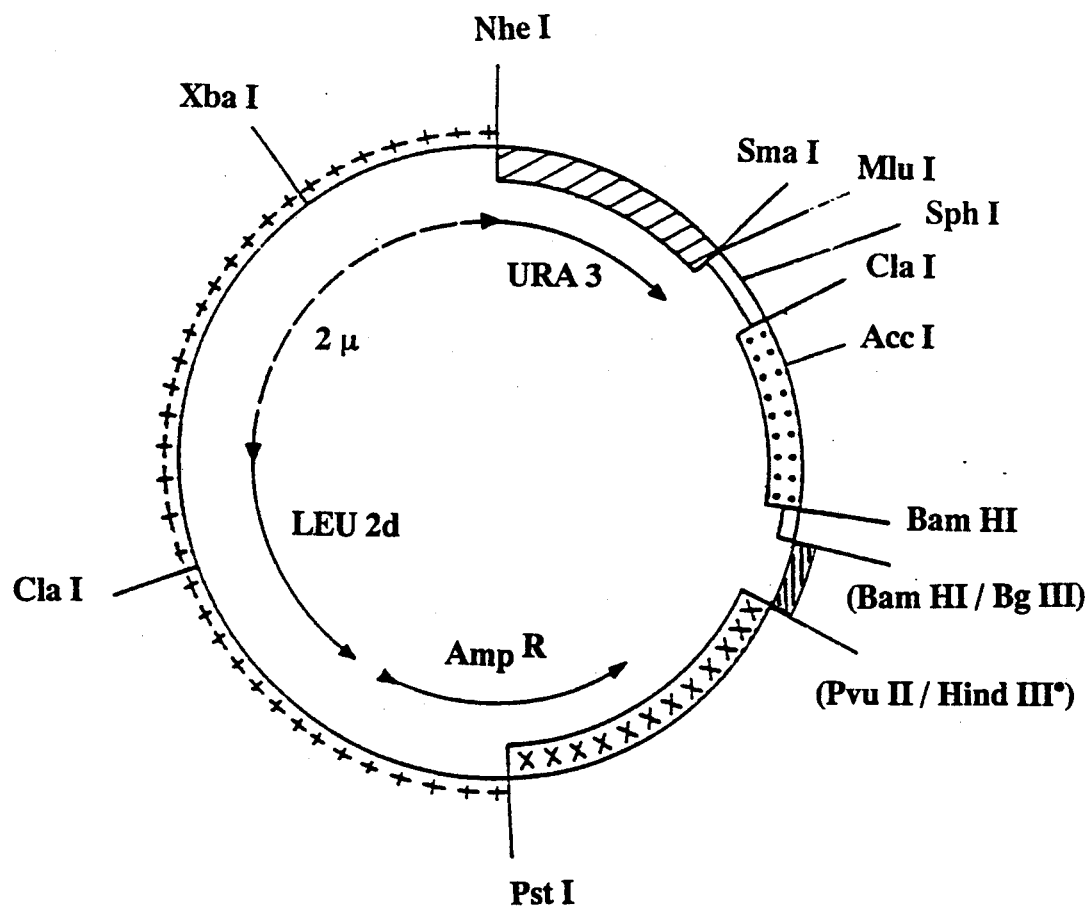
Figure 7:
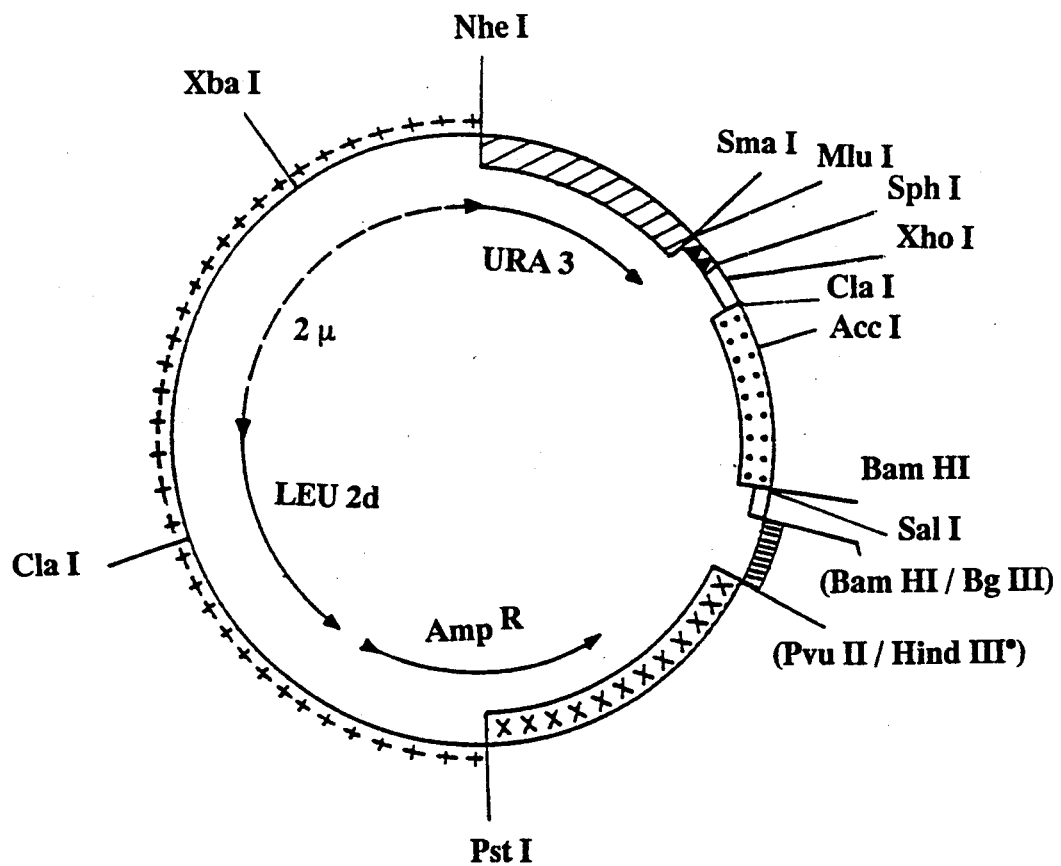
Figure 8:
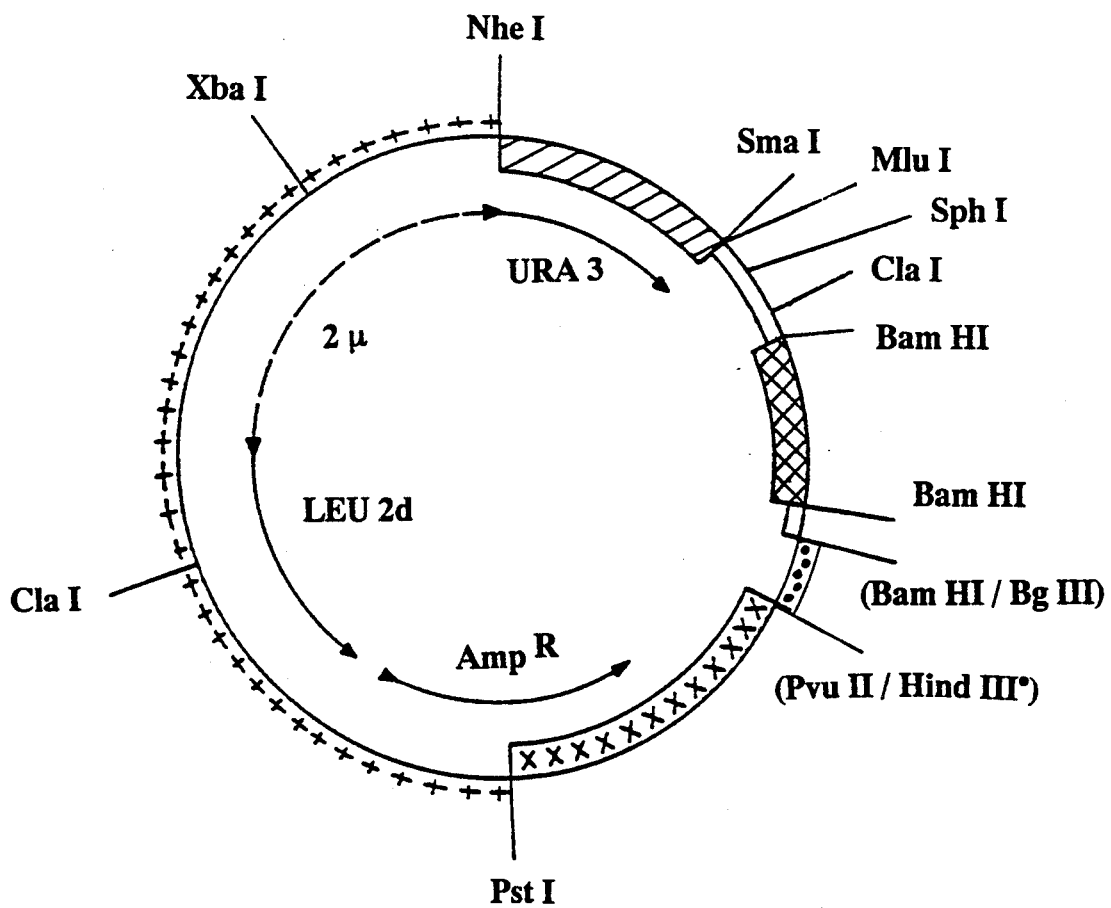
Figure 9:
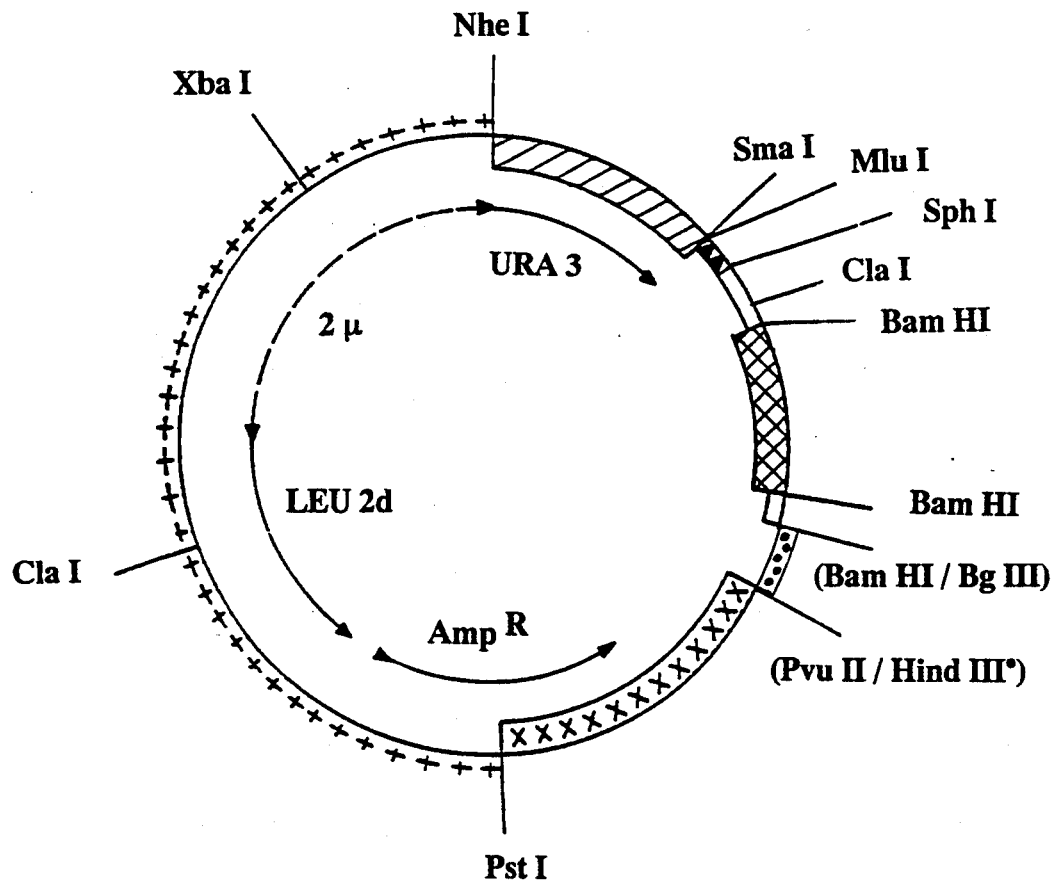
Figure 10:
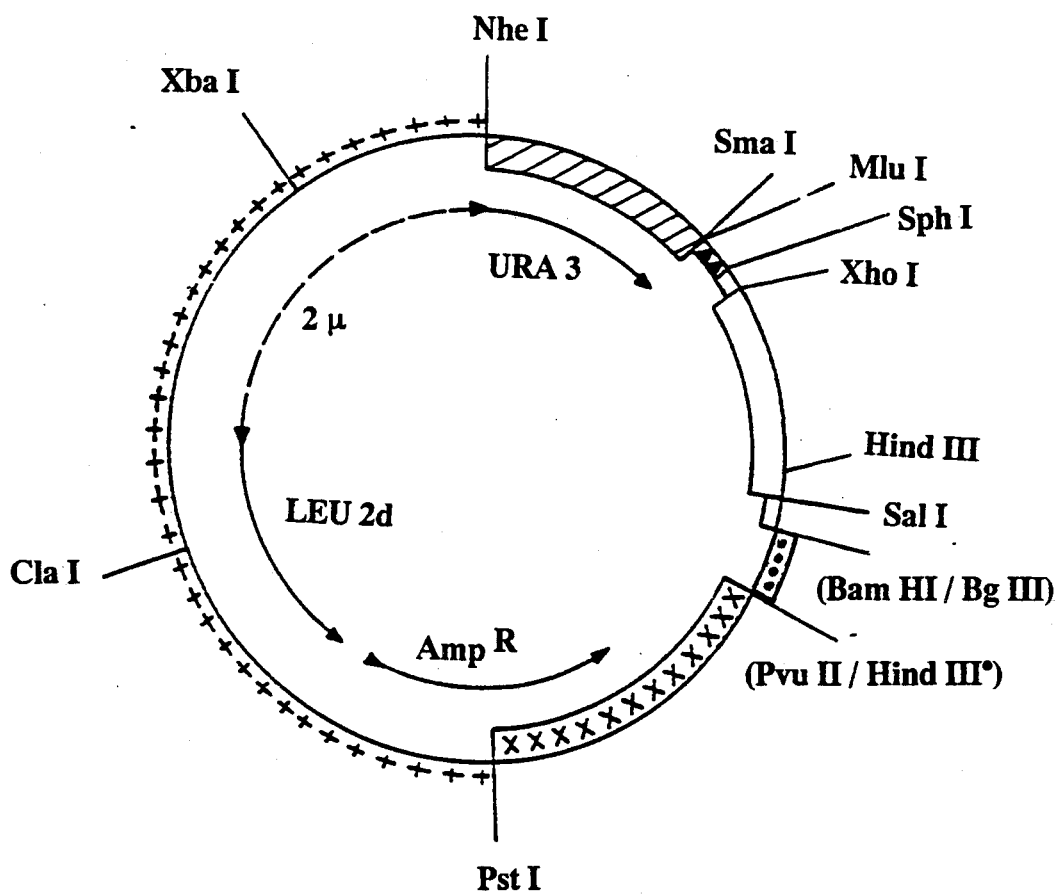
Figure 11:
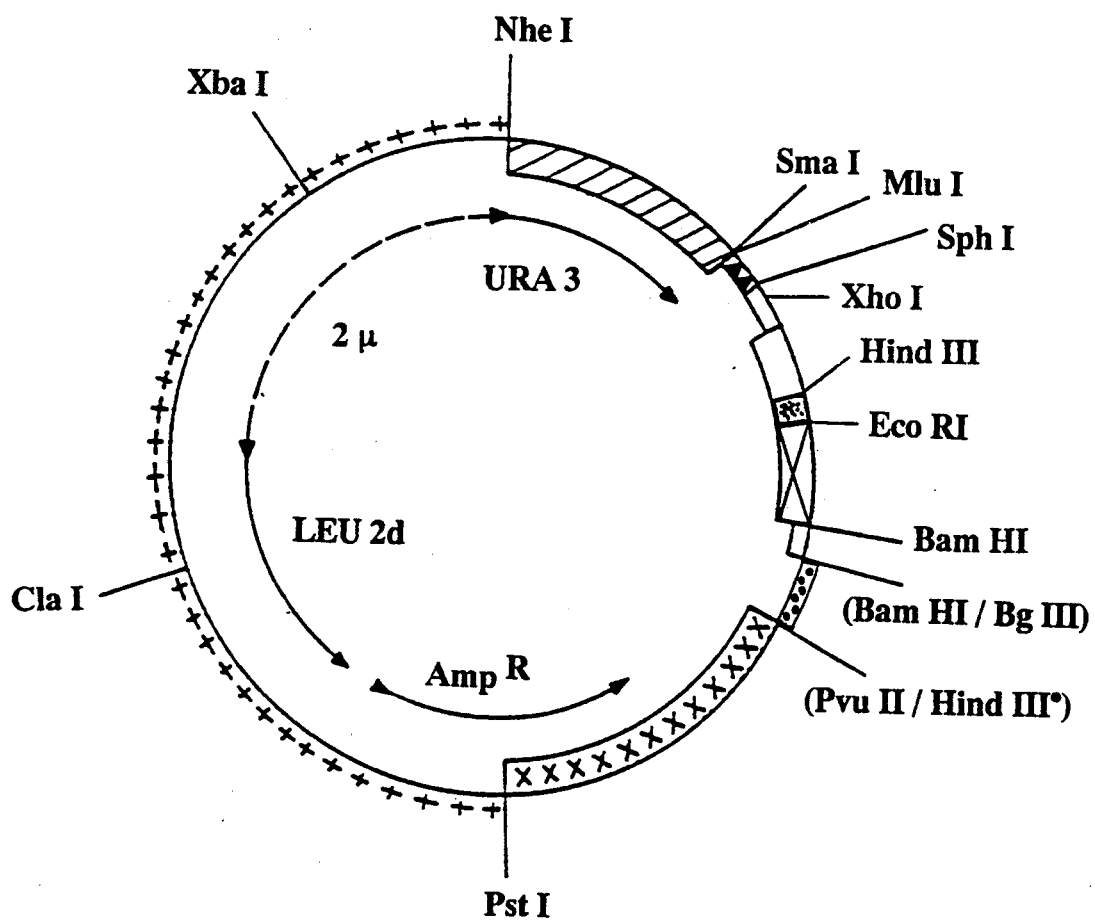

FIG. 5 shows plasmid pEMR 414.
FIG. 6 shows plasmid pEMR 469.
FIG. 7 shows plasmid pEMR 473.
FIG. 8 shows plasmid pEMR 429.
FIG. 9 shows plasmid pEMR 461.
FIG. 10 shows plasmid pEMR 530.
FIG. 11 shows plasmid pEMR 583.

DESCRIPTION OF THE PREFERRED EMBODIMENTS

The invention is illustrated, without implying a limitation, by means of the Examples below:

Many of the following techniques, which are well known to those skilled in the art, are described in detail in the work by Maniatis et al.: "Molecular cloning: a laboratory manual" published in 1984 by Cold Spring Harbor Press in New York.

The synthesis of the oligonucleotides is carried out by means of a DNA Synthetize Biosearch 4600.

EXAMPLE 1

Determination of the sequence of the cDNA of *A. flavus* urate oxidase

1) Isolation of the messenger RNA's from *Aspergillus flavus*

The strain of *A. flavus* which produces urate oxidase was cultivated under conditions appropriate for the production of urate oxidase, i.e. in a medium containing uric acid and having the following composition: glucose 15 g/l, $MgSO_4.7H_2O$ 1 g/l, $KH_2PO_4$ 0.75 g/l, $CaCO_3$ 1.2 g/l, uric acid 1.2 g/l, KOH 0.5 g/l, soy bean oil 0.66 ml/l, $FeSO_4.7H_2O$ 10 mg/l, $CuSO_4.5H_2O$ 1 mg/l, $ZnSO_4.7H_2O$ 3 mg/l, $MnSO_4.H_2O$ 1 mg/l. The medium is adjusted to pH 7 with $H_2SO_4$ 1M and sterilized at 120° C. for 80 min.

In a 5 l Erlenmeyer flask, 1.5 l of medium are inoculated with about 1 to $3.10^7$ spores.

The culture is incubated for about 40 h at 30° C., with agitation (120 rpm). The mycelium is recovered by filtration on gauze, washed with water and frozen in liquid nitrogen.

15 g of mycelium (wet weight) are thawed, resuspended in 45 ml of lysis buffer and then taken up in the same volume of beads (0.45 μm in diameter). The lysis buffer consists of guanidine thiocyanate 4M, Tris-HCl 10 mM pH 7.6, EDTA 10 mM, β-mercaptoethanol 50 ml/l. The mycelian suspension is ground in a Zellmühler mill (vibrogenic) for 5 min.

The ground material is recovered and the beads are decanted. The supernatant is removed (about 45 ml), brought back to a final concentration of 3M in respect of lithium chloride and stored at 0° C.

After two days, it is centrifuged for 60 min at 10,000 rpm. The supernatant is discarded and the residue is taken up in 40 ml of LiCl 3M and centrifuged again at 10,000 rpm for 1 h 30 min.

The following are added: proteinase K (SIGMA) 40 μg/ml, SDS (0.1% w/v) and EDTA 20 mM. The mixture is incubated at 37° C. for 3 h. Precipitation with 2 volumes of ethanol is followed by washing with 70% ethanol. The residue is taken up in 0.5 ml of TE buffer (Tris-HCl 10 mM, EDTA 1 mM pH 7.5), the mixture is extracted twice with chloroform and precipitation is carried out with ethanol. The RNA's are stored at −80° C. in alcohol.

2) Purification of the poly A+ fraction of the RNA's

About 1 mg of RNA is precipitated for 20 min at 4° C. (15,000 rpm) and then washed with 70% ethanol and dried. The residue is taken up in 1 ml of TE buffer and resuspended by agitation in a Vortex. Oligo dT-cellulose type 3 (marketed by Collaborative Research Inc., Biomedicals Product Division) is prepared according to the manufacturer's recommendations. The RNA is deposited on the oligo dT, agitated gently to resuspend the beads and then heated for 1 min at 65° C.

The suspension is adjusted to 0.5M NaCl and then agitated gently for 10 min. It is then centrifuged for 1 min at 1000 rpm, the supernatant is removed and the residue is washed twice with 1 ml of TE buffer containing 0.5M NaCl. The supernatants are removed. The polyadenylated fraction of the RNA's (consisting of the messenger RNA's) is eluted by suspending the beads in 1 ml of TE buffer, then heating this suspension at 60° C. for 1 min and subsequently agitating it for 10 min on a tilting plate. It is then centrifuged for 1 min at 1000 rpm, which makes it possible to recover on the one hand the supernatant containing free mRNA's in solution, and on the other hand the residue of cellulose beads. The above series of operations (starting from elution) is repeated. The supernatants obtained in this way are pooled, the excess beads are removed by centrifugation and the supernatant is precipitated with ethanol containing NaCl in accordance with the usual techniques (Maniatis: op. cit.).

3) Building of the cDNA library.

The messenger RNA's isolated as described in the previous section were used to build a cDNA library in vector pTZ19R (marketed by PHARMACIA). This vector is a plasmid comprising a polylinker containing unique restriction sites.

The cloning technique used is the one described by Caput et al. (primer-adapter technique: Caput et al., Proc. Natl. Acad. Sci. (U.S.A.) (1986) 83, 1670–1674).

It consists firstly in digesting the vector with Pst1, adding a polydC tail to the protuberant 3' end and then digesting the resulting plasmids with BamHI. The fragment corresponding to the vector is purified on a column of Sepharose CL4B (Pharmacia). It therefore comprises a polydC tail at one end, the other end being a sticky end of the BamHI type. Secondly, the messenger RNA's are subjected to reverse transcription starting from a primer having the sequence (SEQ ID NO: 4) 5'<GATCCGGGCCCT$_{(12)}$)<3. Thus the cDNA's have at their 5' end the sequence GATCC complementary to the BamHI sticky end.

The RNA-DNA hybrids obtained by the action of reverse transcriptase are subjected to alkaline hydrolysis, enabling the RNA to be removed. The single-stranded cDNA's are then purified by 2 cycles on a column of Sepharose CL4B and subjected to a treatment with terminal transferase so as to add polydG's at the 3' end. The cDNA's are inserted in single-stranded form into the vector prepared as described above. A second oligonucleotide, the adapter, complementary to the primer, is necessary in order to generate an "open" BamHI site at the 5' end of the cDNA's. After hybridization of the vector, the cDNA and the adapter, the recombinant molecules are circularized by the action of the ligase of phage T4. The single-stranded regions are then repaired by means of the DNA polymerase of phage T4.

The plasmid pool obtained in this way is used to transform the MC1061 strain for ampicillin resistance (Casabadan, Chou and Cohen, J. Bact. (1980) 143, pages 971–980).

4) Determination of the partial sequence of urate oxidase

An *A. flavus* urate oxidase preparation (SIGMA) was repurified by chromatography on a column of Red-agarose 120 (SIGMA), this being followed by filtration on Ultrogel Aca 44 (IBF), an acrylamide-agarose gel.

Direct amino-terminal sequencing of the protein was attempted in order to obtain information on the amino acid sequence of the purified urate oxidase, making it possible to synthesize the probes necessary for cloning the cDNA. This sequencing was not successful, probably because of amino-terminal blocking of the protein.

The following strategy was therefore developed to obtain the partial sequence of urate oxidase:
cleavage of the protein with proteolytic enzymes (using the enzymes trypsin and protease V8 of *Staphylococcus aureus*)
separation of the resulting polypeptides by reversed phase HPLC
sequencing of the purified peptides.

1) Hydrolysis of the urate oxidase with trypsin, purification and sequencing of the peptides:

The urate oxidase, at a concentration of 9 mg/ml in an ammonium carbonate buffer 100 mM pH 8.9, was digested with trypsin (Worthington, TPCK), in a ratio urate oxidase/trypsin of 30/1 by weight, at 30° C. for 24 h. After tryptic hydrolysis, 60 µg of digested urate oxidase were directly injected on to a reversed phase HPLC column of Brownlee G18 grafted silica (column: 10×0.2 cm) equilibrated with acetonitrile 1% (v/v) and trifluoroacetic acid 0.1% (v/v) in water. The peptides were then eluted by a linear gradient of acetonitrile in a solution of trifluoroacetic acid (0.1% v/v) in water, varying from 1% to 60% of acetonitrile in 60 min, at a rate of 150 µl/min. The peptides leaving the column were detected by measurement of the optical density at 218 nm.

Figure 1:
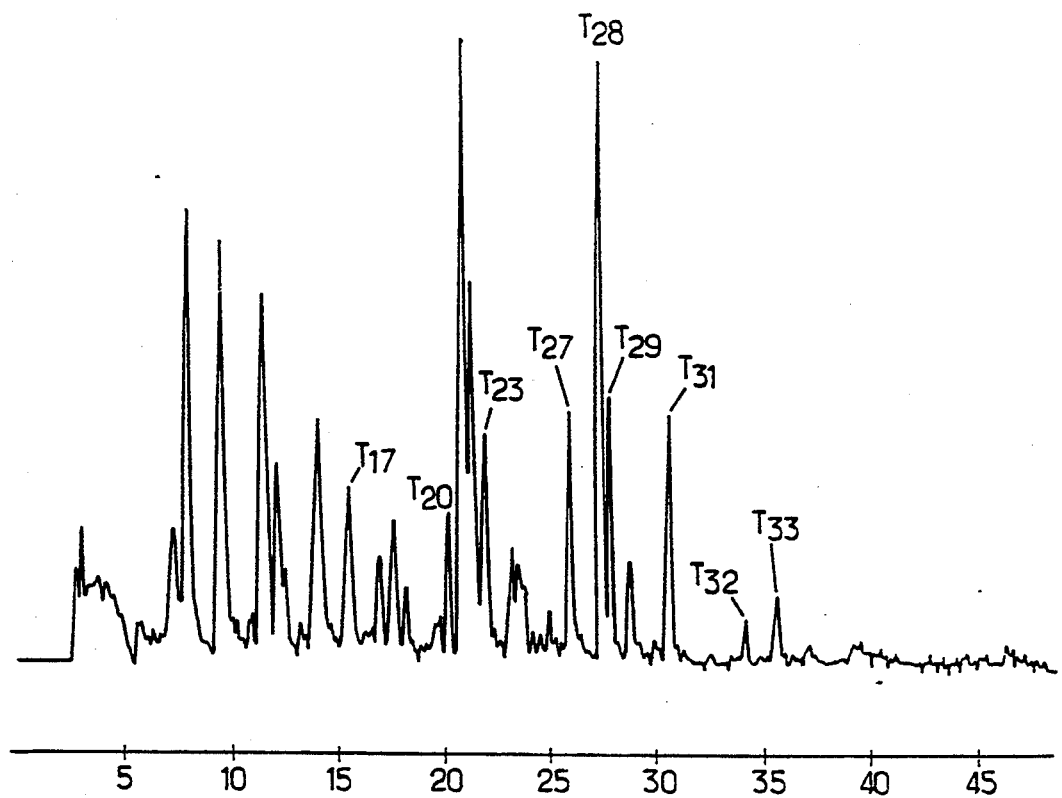
FIG. 1 shows the elution profile of the product of tryptic digestion of urate oxydase, measured by the optical density at 218 nm.

The elution profile is shown in FIG. 1, in which the numbers following the letter T (trypsin) correspond to the peaks identified.

Each peak was collected and stored at −20° C. until analyzed on a protein sequencer (model 470 A from Applied Biosystems) equipped with a chromatograph (model 430 A from Applied Biosystems), which continuously analyzes the phenylthiohydantoic derivatives formed, after each degradation cycle.

Table (1) below shows the peptide sequences (SEQ ID NOS: 5–13) of the 9 peaks identified.

2) Hydrolysis of the urate oxidase with protease V8, purification and sequencing of the peptides:

The urate oxidase, at a concentration of 2 mg/ml in an ammonium acetate buffer 100 mM pH 6.8, was digested with the protease V8 of *Staphylococcus aureus* (Boehringer-Mannheim), in a ratio urate oxidase/-protease V8 of 60/1, at 30° C. for 72 h. 160 µg of digested urate oxidase were then injected on to a reversed phase HPLC column of Brownlee G18 grafted silica (column: 10×0.2 cm; particles: 7×0.03 µm), equilibrated with acetonitrile 1% and trifluoroacetic acid 0.1% (v/v) in water. The peptides were then eluted by a linear gradient of acetonitrile in a solution of trifluoroacetic acid in water (0.1% (v/v)), varying from 1% to 60% of acetonitrile in 60 min, at a rate of 150 µl/min. The peptides leaving the column were detected by measurement of the optical density at 218 nm.

Figure 2:
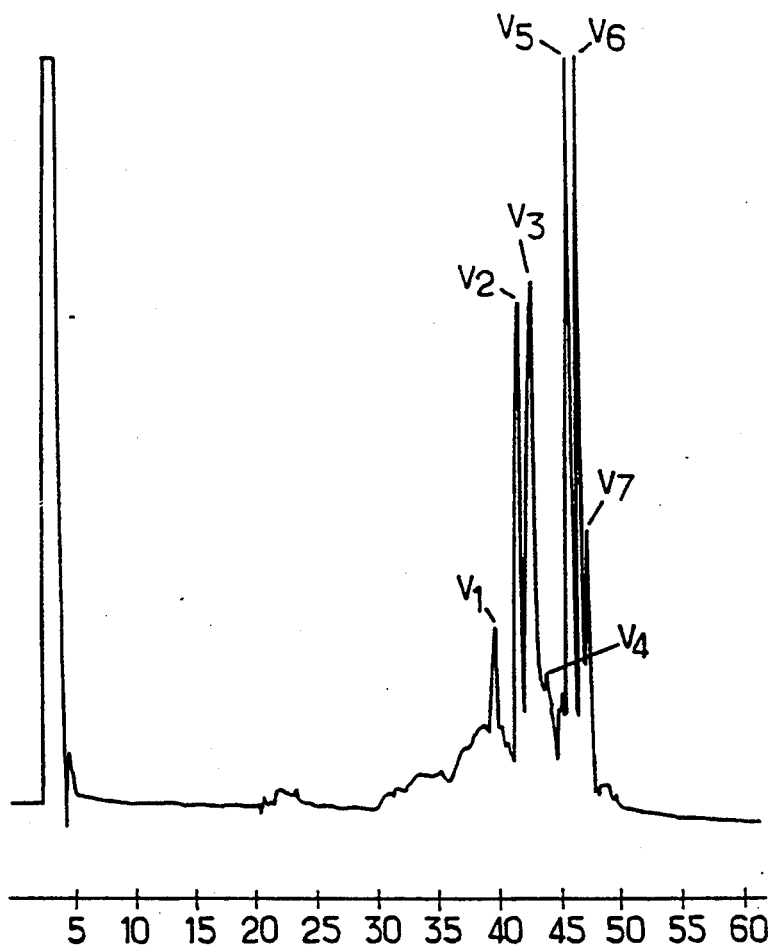
FIG. 2 shows the elution profile of the product of tryptic digestion by protease V8 of urate oxydase, measured by the optical density at 218 nm.

The elution profile is shown in FIG. 2, in which the numbers following the letter V (protease V8) correspond to the peaks identified.

Each peak was collected and stored at −20° C. until analyzed on the protein sequencer already mentioned.

Table (1) below shows the peptide sequences (SEQ ID NOS: 14–18) of the 5 peaks identified.

TABLE 1

Sequencing of the products obtained by hydrolysis

With the aid of trypsin

TABLE 1-continued

| | | Sequencing of the products obtained by hydrolysis |
|---|---|---|
| T17 | (SEQ ID NO: 5) | Asn—Val—Gln—Val—Asp—Val—Val—Glu—Gly—Lys |
| T20 | (SEQ ID NO: 6) | Asn—Phe—Ser—Gly—Leu—Gln—Glu—Val |
| T23 | (SEQ ID NO: 27) | Phe—Asp—Ala—Thr—Trp—Ala |
| T27 | (SEQ ID NO: 8) | His—Tyr—Phe—Glu—Ile—Asp—Leu—Ser |
| T28 | (SEQ ID NO: 4) | Ile—Leu—Ser—Thr—Asp—Val—Asp—Ala—Thr—Trp—Gln—Trp—Lys |
| T29 | (SEQ ID NO: 10) | His—Tyr—Phe—Glu—Ile—Asp—Leu—Ser—Trp—His—Lys |
| T31 | (SEQ ID NO: 11) | Ser—Thr—Asn—Ser—Gln—Phe—Trp—Gly—Phe—Leu—Arg |
| T32 | (SEQ ID NO: 12) | Gln—Asn—Pro—Val—Thr—Pro—Pro—Glu—Leu—Phe—Gly—Ser—Ile—Leu—Gly—Thr |
| T33 | (SEQ ID NO: 13) | Gln—Asn—Pro—Val—Thr—Pro—Pro—Glu—Leu—Phe—Gly—Ser—Ile—Leu—Gly—Thr |
| With the aid of protease V8 | | |
| V1 | (SEQ ID NO: 14) | Tyr—Ser—Leu—Pro—Asn—Lys—His—Tyr—Phe—Glu—Ile—Asp—Leu—Ser—Trp—His—Lys |
| V2 | (SEQ ID NO: 15) | Val—Thr—Leu—Lys—Thr—Phe—Ala—Glu—Asp—Asn—Ser—Ala—Ser—Val—Gln—Ala |
| V3 | (SEQ ID NO: 16) | Thr—Ser—Tyr—Thr—Lys—Asp—Asn—Ser—Ile—Asp—Thr—Asp—Ser—Lys—Asn—Thr—Tyr—Thr |
| V5 | (SEQ ID NO: 17) | Gly—Lys—Gly—Ile—Asp—Ile—Lys—Ser—Ser—Leu—Ser—Gly—Leu—Thr—Val—Leu—Lys—Ser—Thr—Asn—Ser—Gln—Phe—Trp—Gly—Phe—Leu—Arg |
| V6 | (SEQ ID NO: 18) | Gly—Lys—Gly—Ile—Asp—Ile—Lys—Ser—Ser—Leu—Ser—Gly—Leu—Thr—Val—Leu—Lys |

5) Screening of the bacteria 1) preparation of the labeled probes:

Two pools of probes deduced from amino acid sequences of the protein were synthesized with the aid of a Biosearch 4600 DNA synthesizer. The first pool corresponds to the sequence of residues His-Tyr-Phe-Glu-Ile-Asp (amino acid residues 1-6 of SEQ NO: 8), i.e. from 5' to 3' (SEQ ID NO: 19):

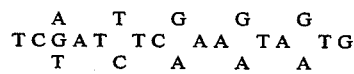

This pool in fact consists of $2^4 \times 3 = 48$ different oligonucleotides, representing all the possible combinations.

The second pool corresponds to the sequence of amino acid residues Gln-Phe-Trp-Gly-Phe-Leu, i.e. from 5' to 3' (SEQ ID NO: 20):

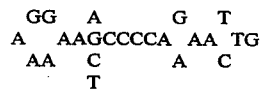

This pool consists of $2^4 \times 4 = 64$ combinations.

The probes are labeled with terminal deoxynucleotide transferase (TdT) (marketed by IBI, Inc.).

The reaction is carried out on 100 ng of a mixture of oligonucleotides in solution (100 mg/ml) in "Cobalt" reaction buffer (supplied as a 10-fold concentrate by IBI, Inc.): 1.4M potassium cacodylate—pH 7.2, 300 mM dithiothreitol, 1 µl of the enzyme terminal deoxynucleotide transferase (IBI, Inc.) and 50 µCi of deoxycytidyl triphosphate, dCTP, labeled with P32.

The reaction is carried out at 37° C. for 10 min and is then stopped by the addition of 1 µl of EDTA 0.5M.

A phenol extraction is carried out and the extract is dialyzed on a column of Biogel P10 polyacrylamide (Biorad: 150–1050).

2) Hybridization and detection of the colonies containing urate oxidase cDNA:

About 40,000 colonies are screened by the in situ hybridization technique developed by Grunstein and Hogness (1975, Proc. Natl. Acad. Sci. (U.S.A.), 72, 3961). About 6000 bacteria are plated out in Petri dishes to give isolated colonies. After incubation for 24 h at 37° C., each dish is replicated on 2 filters, each filter being intended to be treated with one of the 2 pools of probes, so that all the colonies obtained are tested with the 2 pools of probes in parallel.

The filters are hybridized with one of the 2 pools of probes in a buffer containing 6×SSC, 10×Denhardt's solution and 100 µg/ml of sonicated and denatured salmon sperm DNA (SIGMA). The hybridization is carried out at a temperature of 42° C. for 16 h. The 6×SSC solution is obtained by diluting a 20×SSC solution. The preparation of the 20×SSC buffer is described by Maniatis, Fritsch and Sambrook (op. cit.). In summary, this buffer contains 175.3 g/l of NaCl and 88.2 g/l of sodium citrate and is adjusted to pH 7 with a few drops of NaOH 10N, The 10×Denhardt's solution contains 1 g of Ficoll, 1 g of polyvinylpyrrolidone and 1 g of human serum albumin per 500 ml of final volume.

After washing in the 6×SSC solution at 42° C. (3 h with 5 changes of bath), the filters are wiped with Joseph paper and subjected to autoradiography. The filters are developed after 16 h. A fraction of about 0.5% of the colonies was found to have hybridized with the 2 pools of probes.

5 colonies from this fraction were taken up and purified. The plasmid DNA was prepared from each of these colonies and this DNA was analyzed by digestion with either BamHI, or HindIII, or both BamHI and HindIII.

After analysis on agarose gel, the 5 plasmids obtained were found to have been linearized by BamHI and by HindIII. The double digestions make it possible to release a fragment corresponding to the whole of the cloned cDNA. The size of this fragment is about 1.2 kb in 3 cases and about 0.9 kb in the other 2 cases. For the following determination, one of the 0.9 kb fragments and one of the 1.2 kb fragments were selected and recloned (see section 6 below).

6) Determination of the sequence of urate oxidase cDNA

On the one hand one of the 0.9 kb fragments (clone 9A) and on the other hand one of the 1.2 kb fragments (clone 9C) were recloned in the DNA of the replicative form of single-stranded phage M13. The DNA of the M13 clones, containing the 0.9 kb fragment on the one hand and the 1.2 kb fragment on the other, was digested with exonuclease so as to generate a series of overlapping M13 clones (procedure: "Cyclone I Biosystem" of IBI). Said clones were sequenced by the dideoxyribonucleotide method (Sanger et al., PNAS-U.S.A.—1977, 14, 5463–5467).

The nucleotide sequence of clone 9C (SEQ ID NO: 36) is shown in FIGS. 3A and 3B, which also indicates, with an arrow, the start of clone 9A and, with a nucleotide symbol followed by an asterisk*, the sequenced nucleotides of clone 9A which are not identical to those of clone 9C (when matching the two sequences and the AccI and BamHI restriction sites used in the subsequent constructions (cf. 2)).

It is found that:
the nucleotide sequence of the longer fragment (clone 9C) overlaps that of the shorter fragment (clone 9A) but for two differences (see FIGS. 3A and 3B). One of the differences is quiescent and the other corresponds to a change from a tryptophan residue to a glycine residue. These differences may be due either to differences in the messenger RNA's isolated (cf. 2) above) or to errors in the reverse transcriptase used when building the cDNA library (cf. 3) above).

In the case of the longer fragment, an ATG codon (in position 109 in FIGS. 3A and 3B) opens an open reading frame corresponding to a polypeptide of 302 amino acids, with a molecular weight of about 34,240 Da, whose sequence corresponds to the partial sequence of purified *A. flavus* urate oxidase (cf. 4)).

FIGS. 4A and 4B show the DNA sequence opened by the ATG codon and the polypeptide coded for, and, with arrows opposite the polypeptide coded for, the sequenced peptides (cf. 4)) obtained by hydrolysis of *A. flavus* urate oxidase with trypsin and protease V8.

It is found that the sequence of the polypeptide terminates in the triplet Ser-Lys-Leu, which is typical of peroxisomal location enzymes (Gould S. J. et al., J. Cell. Biology 108 (1989) 1657–1664).

EXAMPLE 2

Construction of three expression vectors for urate oxidase cDNA in yeast: plasmid pEMR469 carrying an ADH2 promoter, and plasmid pEMR473 and plasmid pEMR515 carrying the artificial promoter of the invention The strategy employed uses fragments obtained from pre-existing plasmids available to the public, and fragments prepared synthetically by the techniques now in common use. The cloning techniques employed are those described by T. MANIATIS, E. F. FRITSCH and J. SAMBROOK in "Molecular Cloning, a laboratory manual" (Cold Spring Harbor Laboratory, 1984). The oligonucleotides are synthesized with the aid of a Biosearch 4600 DNA synthesizer.

The following description will be understood more clearly with reference to FIGS. 5, 6 and 7, which respectively show restriction maps of plasmids pEMR414, pEMR469 and pEMR473. The symbols used in these Figures will be specified in the description below. In the case where a site has been blunted by Klenow polymerase, it carries the index "°"; where the sites have been eliminated by ligation, they are indicated in brackets.

1) Construction of plasmid pEMR469:

This plasmid was constructed from the shuttle vector *E. coli*-yeast pEMR414, constructed by successive ligations of the following components:

the PstI-HindIII° fragment—symbolized by ± ± ± in FIG. 5—of plasmid pJDB207 (BEGGS, 1978: Gene cloning in yeast—p. 175–203 in: Genetic Engineering, vol. 2—WILLIAMSON—Academic Press—London UK), comprising the upstream part of the ampicillin resistance gene $Amp^R$ of pBR322 (Sutcliffe, 1979, Cold Spring Symp. Quart. Biol. 43, 779) and an endogenous 2μ fragment, B form, carrying the LEU2 gene of *S. cerevisiae* partially modified by the deletion of its promoter (called LEU2d), the locus STB (REP3) and the origin of replication of the 2μ fragment (HARTLEY and DONELSON, 1980, Nature, 286, 860–865). The HindIII end of this fragment has been blunted by the action of Klenow polymerase. It is denoted by HindIII° in FIG. 5.

the HindIII-SmaI fragment—represented by ▨ FIG. 5—of yeast chromosome V, containing the URA3 gene with its promoter (ROSE et al., 1984, Gene, 29, p. 113–124). This HindIII-SmaI fragment originates from plasmid pFL1 (CHEVALLIER et al., 1980, Gene 11, 11–19). The HindIII end of this plasmid has been blunted by the action of Klenow polymerase.

an SamI-BamHI fragment—symbolized by═in FIG. 5—containing a synthetic version of the promoter of the ADH2 gene which differs from the natural version described by RUSSEL and SMITH (RUSSEL et al. (1983) J. Biol. Chem. 258, 2674–2682) only by a few base pairs intended for introducing restriction sites. (The natural sequence could be used with only slightly different results.) The sequence of this fragment (SEQ ID NO: 37) is given below:

```
S     M
m     l
a     u
I     I
▼ GGGACGCGTCTCCTCTGCCGGAACACCGGGCATCTCCAACTTATAAGTTGGAG
  -------+---------+---------+---------+---------+---------
  CCCTGCGCAGAGGAGACGGCCTTGTGGCCCGTAGAGGTTGAATATTCAACCTC

AAATAAGAGAATTTCAGATTGAGAGAATGAAAAAAAAAAAAAAAAAAAAGGCAGAGGAGA
  -------+---------+---------+---------+---------+---------
TTTATTCTCTTAAAGTCTAACTCTCTTACTTTTTTTTTTTTTTTTTTTTTCCGTCTCCTCT
```

-continued

```
                                          S
                                          p
                                          h
                                          I
GCATAGAAATGGGGTTCACTTTTTGGTAAAGCTATAGCATGCCTATCACATATAAATAGA
----+----------+----------+----------+----------+----------+------
CGTATCTTTACCCCAAGTGAAAAACCATTTCGATATCGTACGGATAGTGTATATTTATCT

GTGCCAGTAGCGACTTTTTTCACACTCGAGATACTCTTACTACTGCTCTCTTGTTGTTTT
----+----------+----------+----------+----------+----------+------
CACGGTCATCGCTGAAAAAAGTGTGAGCTCTATGAGAATGATGACGAGAGAACAACAAAA

TATCACTTCTTGTTTCTTCTTGGTAAATAGAATATCAAGCTACAAAAAGCATACAATCAA
----+----------+----------+----------+----------+----------+------
ATAGTGAAGAACAAAGAAGAACCATTTATCTTATAGTTCGATGTTTTCGTATGTTAGTT

B
                                                              a
              C                                               m
              l                                               H
              a                                               I
              I                                               ▼
CTATCAACTATTAACTATATCGATACCATATGGATCCGTCGACTCTAGAGGATCGTC
----+----------+----------+----------+----------+----------+------
GATAGTTGATAATTGATATAGCTATGGTATACCTAGGCAGCTGAGATCTCCTAGCAG
                B
                a
                m
                H
                l
GACTCTAGAG▼
----------+
CTGAGATCTCCTAG
``` the BgIII-HindIII fragment—symbolized by ■ in FIG. 5—carrying the 3' end of the yeast PGK gene. This fragment originates from complete digestion with BgIII of the HindIII fragment of the yeast chromosomal DNA, carrying the PGK gene described by HITZEMAN et al, (1982, Nucleic Acids Res., 10, 7791-7808), which has only one BgIII site. This digestion makes it possible to obtain two HindIII-BgIII fragments of which the smaller, of about 0.4 kb, which carries the 3' end of the yeast PGK gene, is retained. The sequence of the latter fragment is described by HITZEMANN et al. (op. cit.). The BgIII site is cloned in the BamHI site of the previous fragment (the BamHI and BgIII sites therefore disappearing), and the HindIII site, blunted by the action of Klenow polymerase, is cloned in the PvuII site of the PvuII-PstI fragment of pBR322, described below.

the PvuII-PstI fragment—symbolized by ×× in FIG. 5—of pBR322, containing the origin of replication and the downstream part of the ampicillin resistance gene Amp$^R$.

Plasmid pEMR414 formed in this way therefore contains the following components:

an origin of replication and an ampicillin resistance gene Amp$^R$ permitting the replication and selection of the plasmid in *E. coli* cells. These components permit transformation in *E. coli* cells.

an origin of replication for the yeast (ARS), the locus STB and the LEU2 gene of *S. cerevisiae* without promoter and the URA3 gene of *S. cerevisiae* with its promoter. These components permit the replication and selection of the plasmid in *S. cerevisiae* cells and a sufficient partition efficacy in cells containing the endogenous 2μ plasmid.

Plasmid pEMR414 was completely digested with the restriction enzymes NheI and ClaI. The small NheI-ClaI fragment containing the URA3 gene, hereafter called fragment A, was purified.

Plasmid pEMR414 was completely digested with the enzymes NheI and BamHI. The large NheI-BamHI fragment containing especially the LEU2d gene and the origin of replication of plasmid pBR322, hereafter called fragment B, was purified.

The synthetic ClaI-AccI fragment, containing the start of a gene coding for the protein deduced from the urate oxidase cDNA sequence (clone 9C), was also prepared. This fragment contains modifications, relative to clone 9C, introduced for the purpose of inserting codons which are customary in yeast (q.v. SHARP et al., 1986, Nucl. Ac. Res., vol. 14, 13, pp. 5125-5143) without changing the amino acids coded for. The sequence of this fragment (SEQ ID NO: 22), hereafter called fragment C, is as follows (the underlined nucleotides are those modified relative to clone 9C):

```
   C                                                         A
   l                                                         c
   a                                                         c
   I                                                         I
CGATATACACAATGTCTGCTGTTAAGGCTGCTAGATACGGTAAGGACAACGTTAGAGT
----+----------+----------+----------+----------+----------+------
   TATATGTGTTACAGACGACAATTCCGACGATCTATGCCATTCCTGTTGCAATCTCAGA
```

The plasmid of clone 9C (cf. FIGS. 3A and 3B) was digested with the enzymes AccI and BamHI. The AccI-BamHI fragment, which contains the end of urate oxidase cDNA, hereafter called fragment D, was purified.

This fragment has the following sequence (SEQ ID NO: 23):

Fragments A, B, C and D were ligated to give plasmid pEMR469 shown in FIG. 6, in which the symbols

```
                                              AccI
                                              ▼ CTACAAGGTTCACAAGGACGAGAAG
                                              ----+--------------+--------------+
                                              TGTTCCAAGTGTTCCTGCTCTTC

ACCGGTGTCCAGACGGTGTACGAGATGACC                GTCTGTGTGCTTCTGGAGGGTGAGATTGAG
----+--------------+--------------+           ----+--------------+--------------+
TGGCCACAGGTCTGCCACATGCTCTACTGG                CAGACACACGAAGACCTCCCACTCTAACTC

ACCTCTTACACCAAGGCCGACAACAGCGTC                ATTGTCGCAACCGACTCCATTAAGAACACC
----+--------------+--------------+           ----+--------------+--------------+
TGGAGAATGTGGTTCCGGCTGTTGTCGCAG                TAACAGCGTTGGCTGAGGTAATTCTTGTGG

ATTTACATCACCGCCAAGCAGAACCCCGTT                ACTCCTCCCGAGCTGTTCGGCTCCATCCTG
----+--------------+--------------+           ----+--------------+--------------+
TAAATGTAGTGGCGGTTCGTCTTGGGGCAA                TGAGGAGGGCTCGACAAGCCGAGGTAGGAC

GGCACACACTTCATTGAGAAGTACAACCAC                ATCCATGCCGCTCACGTCAACATTGTCTGC
----+--------------+--------------+           ----+--------------+--------------+
CCGTGTGTGAAGTAACTCTTCATGTTGGTG                TAGGTACGGCGAGTGCAGTTGTAACAGACG

CACCGCTGGACCCGGATGGACATTGACGGC                AAGCCACACCCTCACTCCTTCATCCGCGAC
----+--------------+--------------+           ----+--------------+--------------+
GTGGCGACCTGGGCCTACCTGTAACTGCCG                TTCGGTGTGGGAGTGAGGAAGTAGGCGCTG

AGCGAGGAGAAGCGGAATGTGCAGGTGGAC                GTGGTCGAGGGCAAGGGCATCGATATCAAG
----+--------------+--------------+           ----+--------------+--------------+
TCGCTCCTCTTCGCCTTACACGTCCACCTG                CACCAGCTCCCGTTCCCGTAGCTATAGTTC

TCGTCTCTGTCCGGCCTGACCGTGCTGAAG                AGCACCAACTCGCAGTTCTGGGGCTTCCTG
----+--------------+--------------+           ----+--------------+--------------+
AGCAGAGACAGGCCGGACTGGCACGACTTC                TCGTGGTTGAGCGTCAAGACCCCGAAGGAC

CGTGACGAGTACACCACACTTAAGGAGACC                TGGGACCGTATCCTGAGCACCGACGTCGAT
----+--------------+--------------+           ----+--------------+--------------+
GCACTGCTCATGTGGTGTGAATTCCTCTGG                ACCCTGGCATAGGACTCGTGGCTGCAGCTA

GCCACTTGGCAGTGGAAGAATTTCAGTGGA                CTCCAGGAGGTCCGCTCGCACGTGCCTAAG
----+--------------+--------------+           ----+--------------+--------------+
CGGTGAACCGTCACCTTCTTAAAGTCACCT                GAGGTCCTCCAGGCGAGCGTGCACGGATTC

TTCGATGCTACCTGGGCCACTGCTCGCGAG                GTCACTCTGAAGACTTTTGCTGAAGATAAC
----+--------------+--------------+           ----+--------------+--------------+
AAGCTACGATGGACCCGGTGACGAGCGCTC                CAGTGAGACTTCTGAAAACGACTTCTATTG

AGTGCCAGCGTGCAGGCCACTATGTACAAG                ATGGCAGAGCAAATCCTGGCGCGCCAGCAG
----+--------------+--------------+           ----+--------------+--------------+
TCACGGTCGCACGTCCGGTGATACATGTTC                TACCGTCTCGTTTAGGACCGCGCGGTCGTC

CTGATCGAGACTGTCGAGTACTCGTTGCCT                AACAAGCACTATTTCGAAATCGACCTGAGC
----+--------------+--------------+           ----+--------------+--------------+
GACTAGCTCTGACAGCTCATGAGCAACGGA                TTGTTCGTGATAAAGCTTTAGCTGGACTCG

TGGCACAAGGGCCTCCAAAACACCGGCAAG                AACGCCGAGGTCTTCGCTCCTCAGTCGGAC
----+--------------+--------------+           ----+--------------+--------------+
ACCGTGTTCCCGGAGGTTTTGTGGCCGTTC                TTGCGGCTCCAGAAGCGAGGAGTCAGCCTG

CCCAACGGTCTGATCAAGTGTACCGTCGGC                CGGTCCTCTCTGAAGTCTAAATTGTAAACC
----+--------------+--------------+           ----+--------------+--------------+
GGGTTGCCAGACTAGTTCACATGGCAGCCG                GCCAGGAGAGACTTCAGATTTAACATTTGG

AACATGATTCTCACGTTCCGGAGTTTCCAA                GGCAAACTGTATATAGTCTGGGATAGGGTA
----+--------------+--------------+           ----+--------------+--------------+
TTGTACTAAGAGTGCAAGGCCTCAAAGGTT                CCGTTTGACATATATCAGACCCTATCCCAT

TAGCATTCATTCACTTGTTTTTTACTTCCA                AAAAAAAAAAAAAAAAAAAAAAAAAAAAAA
----+--------------+--------------+           ----+--------------+--------------+
ATCGTAAGTAAGTGAACAAAAAATGAAGGT                TTTTTTTTTTTTTTTTTTTTTTTTTTTTTT

↓ BamHI
AAAAAAAAAAAAAAAAAAAAAAGGGCCCG ▼
----+--------------+--------------+
TTTTTTTTTTTTTTTTTTTTTTCCCGGGCCT    AG₁
``` have the same meanings as in FIG. 5, the novel ClaI-AccI and AccI-BamHI fragments being symbolized by ☷.

Plasmid pEMR469 carries a sequence coding for the protein deduced from the sequence of urate oxidase cDNA, under the control of a promoter called an ADH2 promoter, similar to the natural ADH2 promoter, comprising the sequence (SEQ ID NO: 24)

ment, containing the urate oxidase gene, was then ligated with the synthetic fragment, whose sequence is given below (SEQ ID NO: 1), corresponding to a part (200 bp) of the sequence upstream from the TATA component of promoter GAL7 of S. cerevisiae, said part comprising two high-affinity upstream activation sequences called UAS1 and UAS2, which are boxed off below (q.v. R.J. BRAM et al. (1986) EMBO J., vol. 5, no. 3, p. 603–608).

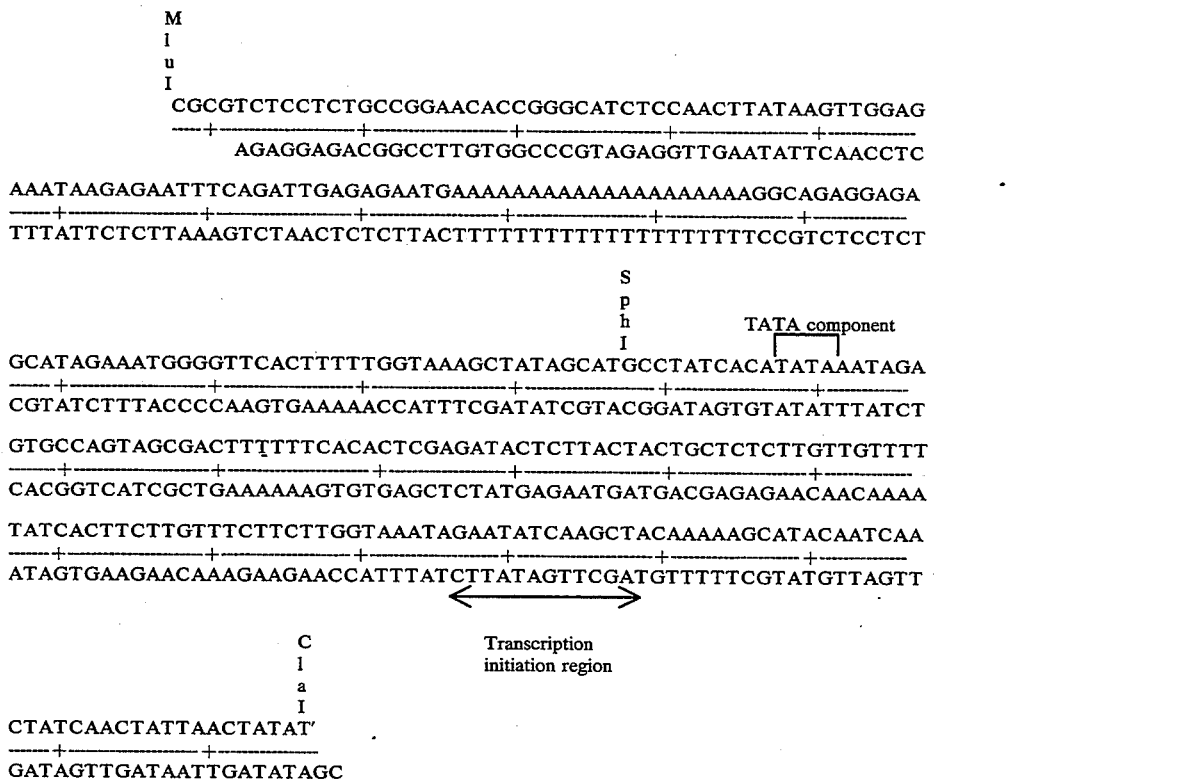

2) Construction of plasmid pEMR473:

Plasmid pEMR469 was completely digested with the enzymes MluI and SphI. The large MluI-SphI frag-

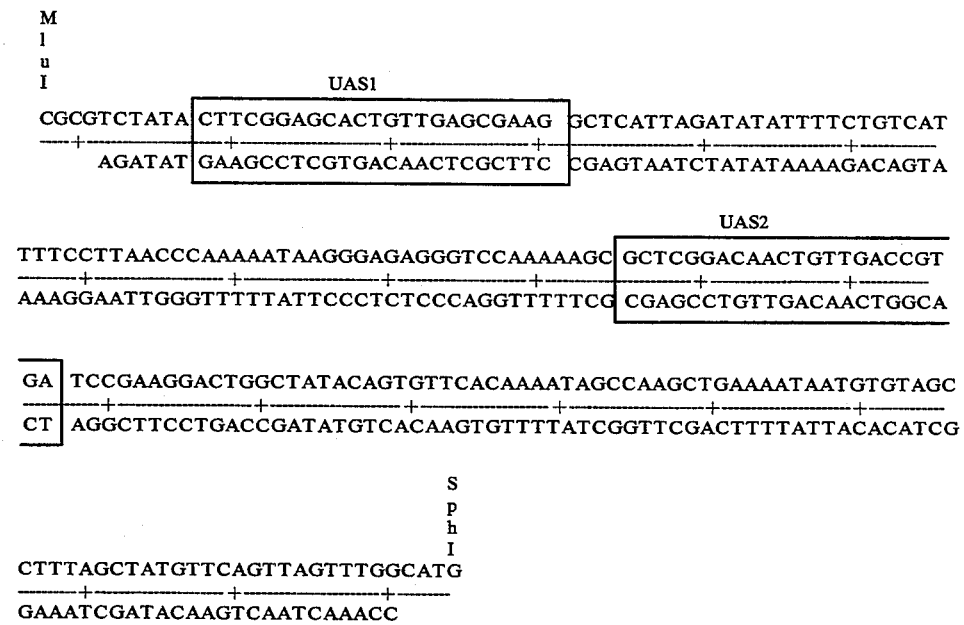

Plasmid pEMR473 obtained in this way is shown in FIG. 7, in which the symbols have the same meanings as in FIG. 6, the novel MluI-SpHI fragment introduced being symbolized by ▒

Plasmid pEMR473 therefore carries a sequence coding for the protein deduced from the sequence of urate oxidase cDNA, under the control of the artificial promoter of the invention, which comprises the sequence (SEQ ID NO: 3)

modified XbaI
▼CTAGGCTAGCGGGCCCGCATGCA
CGATCGCCCGGGCGTACGTGCGC▼
MluI

Plasmid pEMR515 obtained in this way has only one of the three components of the target FRT site of the recombinase coded for by the FLP gene of the 2μ frag-

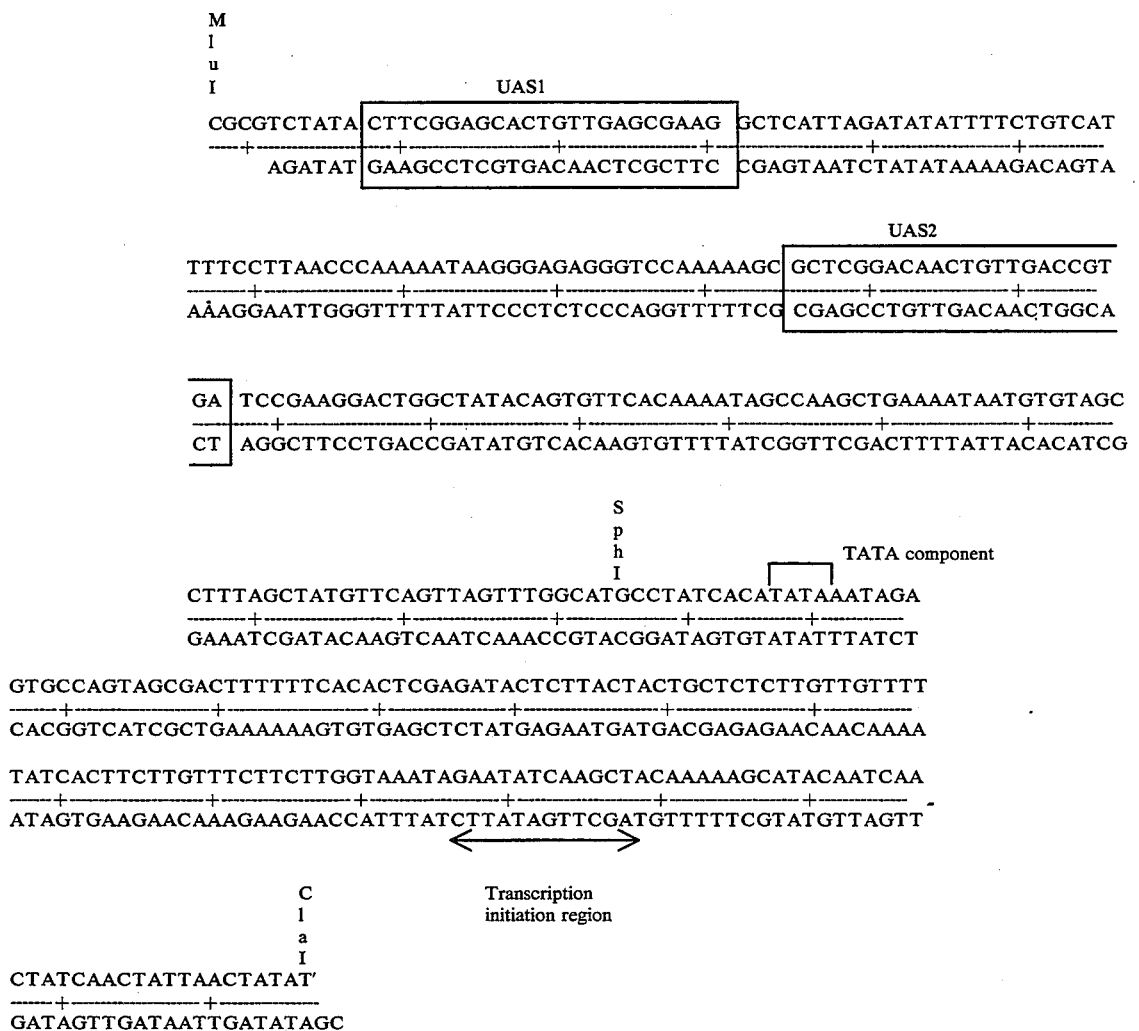

3) Construction of plasmid pEMR515:

Plasmid pEMR473 was partially digested with the enzyme XbaI and totally digested with the enzyme MluI. The large XbaI-MluI fragment was purified. This fragment contains especially the sequences of the origin of replication and the locus STB of the 2μ fragment, the LEU2d gene, the ampicillin resistance gene Amp$^R$, the origin of replication of pBR322 and the expression cassette for urate oxidase. On the other hand, it contains neither the URA3 gene nor that part of the 2μ fragment which is between the XbaI and NheI sites.

The large XbaI-MluI fragment was recircularized via the following sequence adapter containing MluI and modified XbaI sticky ends (SEQ ID NO: 25):

ment.

Plasmid pEMR515 therefore carries a sequence coding for the protein deduced from the sequence of urate oxidase cDNA, under the control of the artificial promoter of the invention.

EXAMPLE 3

Transformation of the EMY761 yeast strain by plasmids pEMR469, pEMR473 and pEMR515—Transformation of the EMY500 and GRF18 yeast strains by plasmid pEMR515—Transformation with selection for the prototrophy of leucine Three non-isogenic strains of Saccharomyces cerevisiae were used as recipient strains:
the EMY761 strain (Matα, leu2, ura3, his3, gal)
the EMY500 strain (Matα, leu2, ura3, pep4)
the GRF18 strain (Matα, leu2, his3)

The GRF18 strain is well known to those skilled in the art (Gerry FINK, MIT, USA). The EMY761 and EMY500 strains are related to the GRF18 strain. They were obtained by successively crossing the GRF18 strain with a ura3 strain derived from the FL100 strain (deposited in the ATCC under no. 28 383) and with the 20B12 strain (Matα, tsp1, pep4) described by E. W. JONES (E. W. JONES et al. (1977) Genetics, 85, 23).

The GRF18 strain can be obtained by curing plasmid pEMR515 of the GRF18 pEMR515 (leu+) strain deposited in the CNCM under reference no. I-920 on 28 Dec. 1989, and the EMY500 strain can be obtained by curing plasmid pEMR515 of the EMY500 pEMR515 (leu+) strain deposited in the CNCM under reference no. I-919 on 28 Dec. 1989.

These strains contain mutations (leu2 and ura3) capable of being complemented by the LEU2d defective selection marker and the URA3 selection marker, which are present in each of plasmids pEMR469 and pEMR473.

The transformation technique used is a variant of that described by Beggs et al. (Beggs et al. (1978), Nature 275, 104–109). It consists in subjecting yeasts to a protoplastization treatment in the presence of an osmotic stabilizer, namely sorbitol at a concentration of 1M.

The precise transformation protocol is specified below:

a) 200 ml of liquid YPG medium (cf. Table I) are inoculated with about $5 \times 10^6$ cells of a culture in the stationary phase, and the culture inoculated in this way is agitated overnight at 30° C.

b) When the density of the culture reaches about $10^7$ cells per ml, the cells are centrifuged at 4000 rpm for 5 min and the residue is washed with sorbitol 1M.

c) The cells are suspended in 5 ml of sorbitol solution 1M containing 25 mM EDTA and 50 mM dithiothreitol, and are incubated for 10 min at 30° C.

d) The cells are washed once with 10 ml of sorbitol 1M and suspended in 20 ml of sorbitol. Zymolase-100T (a preparation obtained by partial purification of *Arthobacter luteus* culture supernatant on an affinity column and containing β-1,3-glucan laminaripentahydrolase, marketed by SEYKAGAKU KOGYO Co. Ltd.) is added up to a final concentration of 20 μg/ml and the suspension is incubated at room temperature for about 15 min.

e) The cells are resuspended in 20 ml of a medium containing sorbitol, called sorbitol YPG medium (cf. Table I below), and incubated for 20 min at 30° C., with gentle agitation.

f) The cells are centrifuged for 3 min at 2500 rpm.

g) The cells are resuspended in 9 ml of transformation buffer (sorbitol 1M, Tris-HCl 10 mM pH 7.5 and CaCl$_2$ 10 mM).

h) 0.1 ml of cells and 5 μl of DNA solution (about 5 μg) are added and the suspension obtained is left for 10 to 15 min at room temperature.

i) 1 ml of the following solution is added: polyethylene glycol PEG 4000 20%, Tris-HCl 10 mM pH 7.5 and CaCl$_2$ 10 mM.

j) 0.1 ml of the suspension obtained in i) is poured into a tube containing leucine-free solid regeneration medium (cf. Table I below) which has been melted beforehand and kept liquid at about 45° C. The suspension is poured into a Petri dish containing a solidified layer of 15 ml of leucine-free solid regeneration medium.

k) Step j) is repeated with the remainder of the cell suspension obtained in h).

The transformed strains start to appear after three days.

A transformed strain EMY761 pEMR469 (leu+), three transformed strains EMY761 pEMR473 (leu+) (clones 1, 2 and 3), a transformed strain EMY761 pEMR515 (leu+), a transformed strain EMY500 pEMR515 (leu+) and a transformed strain GRF18 pEMR515 (leu+) were thus retained.

TABLE I

Principal media used in Examples 3, 4, 4bis, 6 and 7 uracil-free solid medium 6.7 g of Yeast nitrogen base without Amino Acids (from DIFCO)
5.0 g of casein hydrolyzate (Casamino acids from DIFCO)
10 g of glucose
20 g of agar
Mix all the ingredients in distilled water and make up the final volume to 1 l with distilled water.
Autoclave for 15 min at 120° C.

uracil-free liquid medium

Use the formulation of the uracil-free solid medium without the agar. Autoclave for 15 min at 120° C.

leucine-free solid medium 6.7 g of Yeast nitrogen base without Amino Acids (from DIFCO)
20 mg of adenine
20 mg of uracil
20 mg of l-tryptophan
20 mg of l-histidine
20 mg of l-arginine
20 mg of l-methionine
30 mg of l-tyrosine
30 mg of l-isoleucine
30 mg of l-lysine
50 mg of l-phenylalanine
100 mg of l-glutamic acid
150 mg of l-valine
400 mg of l-leucine
20 g of glucose
20 g of agar
Mix all the ingredients in distilled water. Make up the final volume to 1 l with distilled water. Autoclave for 15 min at 120° C. After autoclaving, add 200 mg of l-threonine and 100 mg of l-aspartic acid.

leucine-free solid regeneration medium

Use the formulation of the leucine-free solid medium, mixing in 30 g of agar instead of 20 g and adding 182 g of sorbitol to the mixture.

leucine-free liquid medium

Use the formulation of the leucine-free solid medium without the agar. Autoclave for 15 min at 120° C. After autoclaving, add 200 mg of l-threonine and 100 mg of l-aspartic acid.

liquid YP medium 10 g of yeast extract (Bacto-yeast extract from DIFCO)
20 g of peptone (Bacto-peptone from DIFCO)
Mix the ingredients in distilled water. Make up the final volume to 1 l with distilled water. Autoclave for 15 min at 120° C.

liquid YPG medium

Use the formulation of the liquid YP medium, adding, after autoclaving, glucose at a concentration of 20 g/l.

sorbitol YPG medium

Use the formulation of the liquid YPG medium, adding, after autoclaving, sorbitol at a concentration of 1M.

ethanol-glycerol YP medium

Use the formulation of the liquid YP medium. After autoclaving, add 10 ml of ethanol 100% (1% final concentration) and 30 g of glycerol.

TABLE I-continued

Principal media used in Examples 3, 4, 4bis, 6 and 7 ethanol-glycerol-galactose YP medium
Use the formulation of the liquid YP medium. After autoclaving, add 10 ml of ethanol 100%, 30 g of glycerol and 30 g of galactose.

EXAMPLE 4

Expression of urate oxidase by the EMY761 pEMR469 (leu+) and EMY761 pEMR473 (leu+) (clones 1, 2 and 3) strains—Immunodetection by Western blot—Assay of the urate oxidase activity and the soluble proteins 1) Expression of urate oxidase:
  a) Transformed Strains In a first stage, a colony of each of the EMY761 pEMR469 (leu+) and EMY761 pEMR473 (leu+) (clones 1, 2 and 3) strains was cultured in 25 ml of leucine-free liquid medium (cf. Table I, Example 3). This made it possible to obtain and maintain a large number of copies of plasmids by carrying out the selection for complementation of the leu2 mutation by the LEU2 gene carried by plasmids pEMR469 and pEMR473.

After 22 h at 30° C., with agitation, the two cultures were centrifuged for 10 min at 7000 rpm. The residues were taken up in 10 ml of sterile distilled water and centrifuged again for 10 min at 7000 rpm. Expression of the urate oxidase was induced by taking up the cells in 20 ml of ethanol-glycerol YP medium for the EMY761 pEMR469 (leu+) strain and in 20 ml of ethanol-glycerol-galactose YP medium (cf. Table I, Example 3) for the EMY761 pEMR473 (leu+) strain. The cultures were incubated again at 30° C. for 27 h, with agitation.
  c) Control strain The non-transformed EMY761 strain, i.e. the EMY761 strain without plasmid, was cultivated as above except that the first culture was carried out in liquid YPG medium. It was subjected on the one hand to induction in 10 ml of ethanol-glycerol liquid YP medium and on the other hand to induction in 10 ml of ethanol-glycerol-galactose YP medium.

2) Preparation of the Samples:

a) The cells cultivated in 1a), 1b) and 1c) were centrifuged and the supernatant was removed. The residues were taken up in 10 ml of distilled water and centrifuged for 10 min at 7000 rpm. The residues washed in this way were taken up in about 1 ml of triethyleneamine buffer, TEA, of pH 8.9. About 300 µl of cells taken up in said buffer were lyzed in the presence of glass beads (from 400 to 500 µm in diameter), representing about half the final volume. This mixture was agitated vigorously in a Vortex 4 times for 1 min, the samples being placed in ice for 30 s between grinding operations. The liquid was withdrawn from the tubes with a Pasteur pipette and transferred to a microtube. The glass beads were washed once with about 200 µl of TEA buffer of pH 8.9. The beads were agitated in a Vortex once for 1 min and the liquid was withdrawn with a Pasteur pipette and added to the above lyzate. The lyzate was then centrifuged in a microtube for 5 min at 7000 rpm. The supernatant was cautiously withdrawn and stored at −20° C. for Western blot, assay of the urate oxidase activity and assay of the total soluble proteins. The residue of the lyzed cells was stored separately at −20° C. for Western blot (cf. below).

Furthermore, samples of the cultures prepared in 1a) and 1b) were taken in the following manner before induction: 2 ml of culture were centrifuged for 10 min at 7000 rpm. The residues were taken up in 500 µl of distilled water and centrifuged again for 5 min at 7000 rpm. The residues were taken up in about 200 µl of TEA buffer of pH 8.9 and lyzed as above in the presence of glass beads. The supernatants and the residues of the lyzed cells were stored separately at −20° C. Assay of the oxidase activity and assay of the total soluble proteins were performed on the supernatants.

3) Immunodetection of the urate oxidase by Western blot:
  a) Procedure

The residues and the supernatants of the different samples were subjected to a Western blot—a technique well known to those skilled in the art—which comprises the following steps:

solubilization of the residue by boiling for 10 min in a buffer, called a loading buffer, consisting of Tris-HCl 0.125M pH 6.8, SDS 4%, bromophenol blue 0.002%, glycerol 20%, β-mercaptoethanol 10% (according to the protocol described by LAEMMLI (U. K. LAEMMLI, Nature, 227 (1970), 680–685)) (step performed solely for the residues);

electrophoretic separation of the different proteins contained in the solubilizate, according to the protocol described by LAEMMLI (U. K. LAEMMLI, Nature, 227 (1970), 680–685); and transfer of said proteins contained in the gel on to a nitrocellulose filter (according to the technique of H. TOWBIN et al., Proc. Natl. Acad. Sci. USA 76 (1979) 4350–4354).

Immunodetection, performed according to the technique of BURNETTE (W. W. BURNETTE, Ana. Biochem. 112 (1981) 195–203), involves the following successive operations:

rinsing the nitrocellulose filter for 10 min with a buffer A (Tris-HCl 10 mM, NaCl 170 mM, KCl 1 mM);

bringing the nitrocellulose filter into contact with a buffer B (buffer A with bovine serum albumin added at a rate of 3 g per 100 ml) for 30 min at 37° C.;

bringing the nitrocellulose filter into contact with an immune serum (polyclonal antibodies recognizing A. flavus urate oxidase) for 1 h at 37° C.;

rinsing the nitrocellulose filter with buffer B;

bringing the nitrocellulose filter into contact with a solution of protein G, labeled with iodine 125 at a rate of 0.1 microcurie/ml, for 1 h at 37° C.;

rinsing the filter with buffer A;

drying the filter between two absorbent sheets;

bringing the filter into contact with an X-ray film; and developing the film.

b) Results

It is found that the EMY761 pEMR469 (leu+) and EMY761 pEMR473 (leu+) (clone 1) strains produce a protein with an apparent molecular weight of about 33 kDa, which is recognized by antibodies directed against A. flavus urate oxidase (prepared in rabbits by techniques well known to those skilled in the art: q.v. VAITU-KAITIS et al. (1981) "Methods in enzymology", Academic Press, New York, vol. 73, p. 46) and which is absent from the control strain.

Comparison between the amounts of this protein for the residues and the supernatants makes it possible to deduce that about 80% of said protein is in soluble form in the lyzate.

4) Assay of the urate oxidase activity:

The urate oxidase activity was measured on the supernatants of the lyzed cells.

a) Principle

The conversion of uric acid to allantoin is followed by the decrease in absorbance at 292 nm. The reaction is as follows:

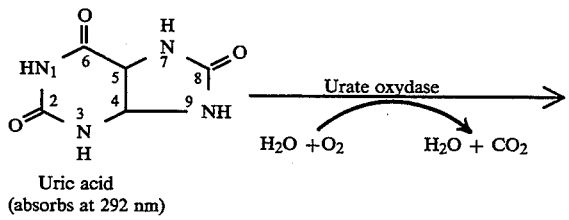

Uric acid
(absorbs at 292 nm)

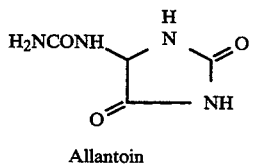

Allantoin b) Reagents a) TEA 0.05M pH 8.9/EDTA buffer 7.5g of TEA (reagent for analysis—Prolabo ref. 287.46.266) are dissolved in 400 ml of distilled water;

0.372 g of Complexon III (Merck—ref. 8418) is dissolved in 50 ml of distilled water;

the two solutions are combined and made up to 500 ml (solution 1);

the pH of this solution is adjusted to 8.9 with HCl 0.2N; and the volume is made up to 1000 ml with distilled water (solution 2).

b) Uric acid stock solution 100 mg of uric acid (Carbiochem—ref. 6671) are dissolved in 50 ml of solution 1;

the pH is adjusted to 8.9 with HCl 0.2N; and the volume is made up to 100 ml with distilled water.

The solution obtained can be stored for one week at 4° C.

c) Uric acid substrate solution 1.5 ml of uric acid stock solution (Carbiochem—ref. 6671) are taken and diluted to 100 ml with TEA buffer (reagent for analysis—Prolabo ref. 287.46.266).

This solution must be used the same day.

c) Procedure

The following volumes are introduced into the quartz cell of a spectrophotometer set to 292 nm and thermostated at 30° C.:

600 μl of uric acid substrate solution (preheated to 30° C.); and

100 μl of the above supernatants to which 200 μl of TEA pH 8.9 have been added (preheated to 30° C.).

After mixing, the change in optical density (sometimes abbreviated to OD hereafter) is read off every 30 s for 5 min. ΔE, the variation in optical density per minute, is deduced from these readings.

d) Expression of the results

The urate oxidase enzymic activity A, expressed in U/ml, is calculated from the ΔE measurement with the aid of the formula $$A = \frac{\Delta E \times V_r \times d}{I \times V_{PE}}$$

in which the symbols $V_r$, $d$, $I$ and $V_{PE}$ respectively represent the reaction volume (0.9 ml), the dilution factor (2), the extinction coefficient of uric acid at 292 nm (12.5) and the volume of the test sample (0.1 ml).

5) Assay of the total soluble proteins in the lyzates:

The protein assay kit from BIORAD was used for assaying the total proteins present in the supernatant of the lyzed cells. It is based on the observation that the maximum absorbance of an acid solution of Coomassie brilliant blue g-250 changes from 465 nm to 595 nm when proteins become attached thereto (q.v. Reisner et al., Anal. Biochem., 64, 509 (1975)).

procedure

The following volumes are introduced into the cell of a spectrophotometer set to 595 nm:

10 μl of sample to which 790 μl of distilled water have been added; and

200 μl of concentrated Dye reagent (Biorad).

The ingredients are mixed and the optical density is read off at 595 nm. A calibration range with increasing concentrations of BSA (bovine serum albumin) was prepared in this way. The unknown concentration of the total proteins in the lyzates is read off on the calibration curve obtained.

6) Results:

The results obtained are collated in Table (II) below, which specifies, for each strain, the culture medium, the carbon and energy source of the culture, the urate oxidase activity in U/ml, the amount of total soluble proteins in mg/ml and the percentage of urate oxidase in the total soluble proteins. This last parameter is calculated by assuming that the specific activity of the recombinant protein is identical to that of the urate oxidase obtained from A. flavus: 30 U/mg.

TABLE II

| Strain | Culture medium at the time of sample preparation | Carbon and energy source of the culture | Urate oxidase activity (U/ml) | Total soluble proteins (mg/ml) | Percentage of urate oxidase in the total soluble proteins |
|---|---|---|---|---|---|
| EMY761 pEMR469 (leu+) | leucine-free liquid medium | glucose | 0.04 | 4.9 | 0.03 |
| EMY761 pEMR473 (leu+) (clone 1) | leucine-free liquid medium | glucose | <0.01 | 3.9 | 0.00 |
| EMY761 pEMR473 (leu+) (clone 2) | leucine-free liquid medium | glucose | <0.01 | 6.0 | 0.00 |
| EMY761 pEMR473 (leu+) (clone 3) | leucine-free liquid medium | glucose | <0.01 | 5.7 | 0.00 |
| non-transformed EMY761 | liquid YPG medium | glucose | <0.01 | 4.5 | 0.00 |
| non-transformed EMY761 | ethanol/glycerol YPG medium | ethanol/glycerol | <0.01 | 4.2 | 0.00 |
| EMY761 pEMR469 (leu+) | ethanol/glycerol YPG medium | ethanol/glycerol | 8.5 | 2.0 | 14 |
| EMY761 pEMR473 (leu+) (clone 3) | ethanol/glycerol YPG medium | ethanol/glycerol | 0.05 | 3.1 | 0.05 |
| EMY761 pEMR473 (leu+) (clone 1) | ethanol/glycerol YPG medium | ethanol/glycerol | 0.05 | 3.1 | 0.05 |
| EMY761 pEMR473 (leu+) (clone 2) | ethanol/glycerol YPG medium | ethanol/glycerol | 0.05 | 3.1 | 0.05 |

TABLE II-continued

| Strain | Culture medium at the time of sample preparation | Carbon and energy source of the culture | Urate oxidase activity (U/ml) | Total soluble proteins (mg/ml) | Percentage of urate oxidase in the total soluble proteins |
|---|---|---|---|---|---|
| non-transformed EMY761 | ethanol/glycerol/galactose YP medium | ethanol/glycerol/galactose | <0.01 | 5.6 | 0.00 |
| EMY761 pEMR473 (leu+) (clone 1) | ethanol/glycerol/galactose YP medium | ethanol/glycerol/galactose | 17.3 | 3.8 | 15 |
| EMY761 pEMR473 (leu+) (clone 2) | ethanol/glycerol/galactose YP medium | ethanol/glycerol/galactose | 36 | 5.7 | 21 |
| EMY761 pEMR473 (leu+) (clone 3) | ethanol/glycerol/galactose YP medium | ethanol/glycerol/galactose | 22 | 4.0 | 18.2 |
| EMY761 pEMR469 (leu+) | ethanol/glycerol/galactose YP medium | ethanol/glycerol/galactose | 10 | 2.4 | 13.5 |

This Table shows that:

a) in the presence of glucose, the ("repressed") level of urate oxidase is not detectable in the case of the artificial promoter of the invention (strain EMY761 pEMR473 (leu+) (clone 1, 2 or 3)), whereas it is detectable in the case of the $ADH_2$ promoter (strain EMY761 pEMR469 (leu+)). In the presence of glucose, therefore, the artificial promoter permits better repression than the $ADH_2$ promoter.

b) in the absence of glucose but in the presence of ethanol/glycerol, the level of urate oxidase is high for the $ADH_2$ promoter (about 14% of the total soluble proteins) and low but detectable for the artificial promoter.

c) in the absence of glucose but in the presence of ethanol/glycerol/galactose, the level of urate oxidase retains a value little different from that of the previous case for the $ADH_2$ promoter (about 13.5% of the total soluble proteins), but reaches a high value (about 18% of the total soluble proteins) for the artificial promoter.

The artificial promoter of the invention therefore permits a high level of production of recombinant protein and has three levels of expression:
zero level a)
basic level b)
maximum level c)

EXAMPLE 4bis

Expression, in an Erlenmeyer flask, of urate oxidase cDNA by the EMY761 pEMR515 (leu+), EMY500 pEMR515 (leu+) and GRF18 pEMR515 (leu+) strains A colony of each of the above three strains was cultured in 20 ml of leucine-free liquid medium.

After one night at 30° C., with agitation, the three cultures were centrifuged for 10 min at 7000 rpm. The cell residues were taken up in 10 ml of sterile distilled water and centrifuged again for 10 min. Expression of the urate oxidase was induced by taking up the cells in 20 ml of ethanol-glycerol-galactose YP medium (cf. Table I, Example 3). The cultures were incubated again at 30° C. for about 20 h, with agitation. As a control, a culture of each non-transformed host strain was prepared.

The cells of each of the six cultures are redeposited by centrifugation and the supernatant is removed. The residues were taken up in 10 ml of distilled water and centrifuged for 10 min at 7000 rpm. The residues washed in this way were taken up in about 1 ml of TEA buffer of pH 8.9 and the grinding and removal of the particles by centrifugation were carried out in the manner described in Example 4, 2). The supernatant of each culture is used, as before, for assay of the urate oxidase and the total proteins. The principal results obtained are collated in Table III. below:

TABLE III

| Strain/culture conditions | Urate oxidase activity (U/ml) | Total soluble proteins (mg/ml) | % of urate oxidase in the soluble proteins |
|---|---|---|---|
| GRF18 pEMR515 (leu+)/a) | <0.1 | 2.2 | <0.05 |
| EMY500 pEMR515 (leu+)/a) | <0.1 | 0.9 | <0.05 |
| EMY761 pEMR515 (leu+)/a) | <0.1 | 1.8 | <0.05 |
| GRF18 pEMR515 (leu+)/b) | 38 | 5.4 | 23 |
| EMY500 pEMR515 (leu+)/b) | 20 | 2.5 | 26 |
| EMY761 pEMR515 (leu+)/b) | 33 | 4.2 | 26 | a): the strains are cultivated in the presence of glucose (non-induction conditions)
b): the strains are cultivated in the absence of glucose and in the presence of galactose (induction)

The promoter according to the invention therefore permits a high level of expression of urate oxidase in three non-isogenic strains.

EXAMPLE 5

Construction of two expression vectors for β-galactosidase in yeast: plasmid pEMR429 carrying an $ADH_2$ promoter, and plasmid pEMR437 carrying the artificial promoter of the invention The strategy employed uses fragments obtained from pre-existing plasmids available to the public, and fragments prepared synthetically by the techniques now in common use. The cloning techniques employed are those described by T. MANIATIS, E. F. FRITSCH and J. SAMBROOK in "Molecular Cloning, a laboratory manual" (Cold Spring Harbor Laboratory, 1984). The oligonucleotides are synthesized with the aid of a Biosearch 4600 DNA synthesizer.

Construction of plasmid pEMR429:

Plasmid pEMR414 (cf. FIG. 5) was completely digested with the restriction enzyme BamHI. The BamHI site, located between the promoter sequences ($ADH_2$) and terminator sequences (PGK), is unique. The linear DNA of the plasmid is purified by elution from an agarose gel after electrophoresis, Plasmid pMC1403 (ref. Casadaban et al. (1980), J. Bacteriol., 143, 971–980) was completely digested with the enzymes BamHI and EcoRI, which made it possible to release a BamHI-EcoRI DNA fragment of about 3 kb containing the essential part (upstream part) of the sequence coding for *E. coli* β-galactosidase. The complete sequence was reconstituted with the aid of the synthetic fragment of the following sequence (SEQ ID NO: 26):

CTACCATTACCAGTTGGTCTGGT
GATGGTAATGGTCAACCAGACCA

GTCAAAAATAATAATAAG
CAGTTTTTATTATTATTCCTAG
                                    BamHI

The BamHI-EcoRI fragment originating from the double digestion of pMC1403 is ligated at EcoRI with the above synthetic fragment.

The BamHI-BamHI fragment obtained is then ligated with the linear DNA of plasmid pEMR414 digested with BamHI, to give plasmid pEMR429 shown in FIG. 8, in which the symbols have the same meanings as in FIG. 5, the BamHI-EcoRI and IcoRI-BamHI fragments introduced being represented by ▬▬.

In this plasmid, the sequence coding for β-galactosidase is under the control of the ADH$_2$ promoter described in Example 2.

2) Construction of plasmid pEMR461:

Plasmid pEMR429 was completely digested with the enzymes MluI and SphI. The large MluI-SphI fragment, containing the β-galactosidase gene, was then ligated with the synthetic fragment whose sequence (SEQ ID NO: 1) given below, comprises the upstream activation sequences (UAS) of the promoter of the GAL7 gene of *S. cerevisiae* and MluI and SphI sticky ends.

```
M
|
u
|
  CGCGTCTATACTTCGGAGCACTGTTGAGCGAAGGCTCATTAGATATATTTTCTGTCAT
- - + - - - - - - - - - - + - - - - - - - - - - + - - - - - - - - - - + - - - - - - - - - - + - - - - - - - - - - + - - - - - -
      AGATATGAAGCCTCGTGACAACTCGCTTCCGAGTAATCTATATAAAAGACAGTA

TTTCCTTAACCCAAAAATAAGGGAGAGGGTCCAAAAAGCGCTCGGACAACTGTTGACCGT
- - - - + - - - - - - - - - - + - - - - - - - - - - + - - - - - - - - - - + - - - - - - - - - - + - - - - - - - - - - + - - - - - -
      AAAGGAATTGGGTTTTTATTCCCTCTCCCAGGTTTTTCGCGAGCCTGTTGACAACTGGCA

GATCCGAAGGACTGGCTATACAGTGTTCACAAAATAGCCAAGCTGAAAATAATGTGTAGC
- - - - + - - - - - - - - - - + - - - - - - - - - - + - - - - - - - - - - + - - - - - - - - - - + - - - - - - - - - - + - - - - - -
      CTAGGCTTCCTGACCGATATGTCACAAGTGTTTTATCGGTTCGACTTTTATTACACATCG

. S
                                p
                                h
                                I
CTTTAGCTATGTTCAGTTAGTTTGGCATG
- - - - + - - - - - - - - - - + - - - - - - - - - - + - - - - -
      GAAATCGATACAAGTCAATCAAACC
```

Plasmid pEMR461 obtained in this way is shown in FIG. 9, in which the symbols have the same meanings as in FIG. 8, the novel MluI-SphI fragment introduced being symbolized by ▬▬.

In this plasmid, the sequence coding for β-galactosidase is under the control of the artificial promoter of the invention, described in Example 2.

EXAMPLE 6

Transformation of the DBY746 *S. cerevisiae* strain by plasmids pEMR429 and pEMR461

Transformation with selection for the prototrophy of uracil:

A colony of the DBY746 strain, which is (Matα, his3, leu2, ura3, trp1, cyh$^R$) (ROSE et al (1981), PNAS USA, 78, 2460–2464), was used to inoculate 100 ml of a medium called liquid YPG medium (cf. Table I of Example 3). When the cell density had reached 10$^7$ cells per ml, the cells were treated with lithium acetate 0.2M for transformation by a technique well known to those skilled in the art and described by ITO et al. (ITO et al., 1983, J. Bacteriology 153, 163–168).

The DBY746 cells were transformed in parallel with about 1 μg of each of plasmids pEMR429 and pEMR461. The transformed cells are selected for the auxotrophic character of uracil (ura+) on a medium called uracil-free solid medium (cf. Table I of Example 3). A transformed strain DBY746 pEMR429 (ura+) and a transformed strain DBY746 pEMR461 (ura+) were thus retained.

EXAMPLE 7

Production of β-galactosidase with the aid of the DBY746 pEMR429 (ura+) and DBY746 pEMR461 (ura+) strains 1) Expression of β-galactosidase:

A transformed colony DBY746 pEMR429 (ura+) and a transformed colony DBY746 pEMR461 (ura+) were each used to inoculate 20 ml of uracil-free liquid medium to which tryptophan (10 mg/l) had been added beforehand. After one night at 30° C., with agitation, 1% of glucose is added and culture is allowed to continue for 4 h. A check is then made to see that there is still some glucose in the cultures. An aliquot is taken in order to assay the β-galactosidase.

After one night at 30° C., with agitation, the two cultures were centrifuged for 10 min at 7000 rpm. The residues were taken up in 10 ml of sterile distilled water and centrifuged again for 10 min at 7000 rpm. Expression of β-galactosidase was induced by taking up the cells in 20 ml of ethanol-glycerol YP medium (cf. Table I, Example 3) for the DBY746 pEMR429 (ura+) strain and in 20 ml of ethanol-glycerol-galactose YP medium (cf. Table I, Example 3) for the DBY746 pEMR461 (ura+) strain. The cultures were incubated again at 30° C. overnight, with agitation.

2) Preparation of the samples and assay:

The cells cultivated above were centrifuged and the supernatant was removed. The residues were taken up in 10 ml of distilled water and centrifuged for 10 min at 7000 rpm. The residues washed in this way were taken up in about 1 ml of β-galactosidase assay buffer (EDTA $2 \times 10^{-3}$M; Na$_2$HPO$_4$ $7 \times 10^{-2}$M; NaH$_2$PO$_4$ $3 \times 10^{-2}$M; MgSO$_4$ $10^{-3}$M; MnSO$_4$ $2 \times 10^{-3}$M). About 300 μl of cells taken up in said buffer were lyzed in the presence of glass beads (from 400 to 500 μm in diameter), representing about half the final volume. This mixture was agitated vigorously in a Vortex 4 times for 1 min, the samples being placed in ice for 30 s between grinding operations. The liquid was withdrawn from the tubes with a Pasteur pipette and transferred to a microtube. The glass beads were washed once with about 200 μl of TEA buffer of pH 8.9. The beads were agitated in a Vortex once for 1 min and the liquid was withdrawn with a Pasteur pipette and added to the above lyzate. The lyzate was then centrifuged in a microtube for 5 min at 7000 rpm. The supernatant was cautiously withdrawn and stored at −20° C. for Western blot, assay of the urate oxidase activity and assay of the total soluble proteins. The residue of the lyzed cells was stored separately at −20° C.

The β-galactosidase activity was assayed by the technique of PARDEE (PARDEE et al., J. Mol. B. (1959), 1, 1656–178).

Furthermore, the total soluble proteins were assayed using the BIORAD protein assay kit, as described in Example 4.

The results obtained are collated in Table IV below:

TABLE IV

| Strain | Carbon and energy source of the mixture | β-Galactosidase activity U/ml | Total soluble proteins μg/ml | Culture medium |
| --- | --- | --- | --- | --- |
| DBY746 pEMR429 (ura+) | glucose | 59 | 375 | Liquid medium without uracil + tryptophan (10 mg/l) + glucose (1%) |
| DBY746 pEMR429 (ura+) | ethanol/glycerol | 6500 | 1700 | ethanol-glycerol YP medium |
| DBY746 pEMR461 (ura+) | glucose | 0 | 350 | liquid medium without uracil + tryptophan (10 mg/l) + glucose (1%) |
| DBY746 pEMR461 (ura+) | ethanol/glycerol/ galactose | 480 | 520 | ethanol-glycerol-galactose YP medium |

This Table shows that:

- in the presence of glucose, the EMY746 pEMR429 (ura+) strain produces a small amount of β-galactosidase, whereas this protein is not detected for the DBY746 pEMR461 (ura+) strain. The artificial promoter of the invention therefore permits better repression than the ADH2 promoter.
- under induction conditions, the artificial promoter leads to a high level of expression of β-galactosidase, although under these conditions it is lower than the level obtained with the ADH2 promoter (SEQ ID NO: 3).

```
              M
              |
              u
              |
CGCGTCTATACTTCGGAGCACTGTTGAGCGAAGGCTCATTAGATATATTTTCTGTCAT
---+----------+----------+----------+----------+----------+-----
AGATATGAAGCCTCGTGACAACTCGCTTCCGAGTAATCTATATAAAAGACAGTA

TTTCCTTAACCCAAAAATAAGGGAGAGGGTCCAAAAAGCGCTCGGACAACTGTTGACCGT
----+----------+----------+----------+----------+----------+-----
AAAGGAATTGGGTTTTTATTCCCTCTCCCAGGTTTTTCGCGAGCCTGTTGACAACTGGCA

GATCCGAAGGACTGGCTATACAGTGTTCACAAAATAGCCAAGCTGAAAATAATGTGTAGC
----+----------+----------+----------+----------+----------+-----
CTAGGCTTCCTGACCGATATGTCACAAGTGTTTTATCGGTTCGACTTTTATTACACATCG

. S
                        p
                        h
                        I
CTTTAGCTATGTTCAGTTAGTTTGGCATGCCTATCACATATAAATAGA
----+----------+----------+-------+----------+------
GAAATCGATACAAGTCAATCAAACCGTACGGATAGTGTATATTTATCT

GTGCCAGTAGCGACTTTTTTCACACTCGAGATACTCTTACTACTGCTCTCTTGTTGTTTT
---+----------+----------+----------+----------+----------+------
CACGGTCATCGCTGAAAAAAGTGTGAGCTCTATGAGAATGATGACGAGAGAACAACAAAA

TATCACTTCTTGTTTCTTCTTGGTAAATAGAATATCAAGCTACAAAAAGCATACAATCAA
---+----------+----------+----------+----------+----------+------
ATAGTGAAGAACAAAGAAGAACCATTTATCTTATAGTTCGATGTTTTTCGTATGTTAGTT

C
                l
                a
                I
CTATCAACTATTAACTATAT
---+----------+------|
```

GATAGTTGATAATTGATATAGC⌐

-continued

EXAMPLE 8

Construction of two vectors for the expression and secretion of the human cytokinin gro-β in yeast: plasmids pEMR575 and pEMR583 carrying the artificial promoter of the invention The Examples described above concern proteins whose localisation is intracellular. Now, it is known that yeast can secrete recombinant proteins in the culture medium. The use of the metabolic pathway leading to secretion of the protein has several important advantages:

1. It enables a reasonably pure and correctly matured product to be recovered from the culture supernatant.
2. It enables the protein to benefit from the modifications associated with the secretion pathway, such as the formation of disulfide bridges, glycosylation etc.

There are several proteins or polypeptides naturally secreted by yeast. In the majority of known cases, these proteins are synthesized in the form of a longer precursor whose NH$_2$-terminal sequence is decisive for entry into the metabolic pathway leading to secretion. In certain cases, these NH$_2$-terminal sequences can be used for the secretion of heterologous proteins. Among these sequences, it is known to use the pre-pro system of the alpha pheromone. The alpha sex pheromone of yeast is a peptide of 13 amino acids which is secreted in the culture medium by S. cerevisiae yeasts of the Matα sex type.

The alpha factor arrests the cells of the opposite sex type (Mata) in the G 1 phase and induces the biochemical and morphological changes necessary for conjugation of the 2 types of cells. Kurjan, J. and Herskowitz, I. (1982), Cell, 30, 933–943, cloned the structural gene of the alpha factor and deduced from the sequence of this gene that this factor of 13 amino acids is synthesized in the form of a pre-pro precursor protein of 165 amino acids. The precursor contains a hydrophobic amino-terminal sequence of 22 amino acids followed by a sequence of 61 amino acids containing 3 glycosylation sites, followed finally by 4 copies of the α factor. These 4 copies are separated by spacer sequences and the mature protein is released from the precursor by virtue of the following enzymic activities:

1. an endopeptidase of the cathepsin B type (product of the KEX2 gene, called yscF) which cleaves Lys-Arg Arg dipeptides at the carboxy terminal end.
2. an exopeptidase of the carboxypeptidase type (product of the KEX1 gene) which cleaves the basic residues at the carboxy terminal end of the excised peptides.
3. a dipeptidylaminopeptidase (called A) (product of the STE13 gene) which removes the Glu-Ala and Asp-Ala doublets.

A first example of a protein which is secreted by this system and uses the promoter of the invention is the human cytokinin gro-β. The cDNA of this protein, which is called either gro-β (S. Haskill et el., 1990, Proc. Natl. Acad. Sci. USA, 87, 7732–7736) or MIP-2α (P. Tekamp-Olson et el., 1990, J. Exp. Med., 172, 911–919) was recently cloned and sequenced. gro-β belongs to a family of cytokinins whose members appear to be involved in modulation of the inflammatory response and in activities of the growth factor type.

The Applicant tested the use of the promoter for the secretion of gro-β by S. cerevisiae. To do this, it replaced the natural signal sequence of gro-β with the pre-pro sequence of the alpha pheromone and placed the precursor of gro-β behind the promoter of the invention.

1) Construction of plasmid pEMR530 (cloning vector):

Plasmid pEMR473 described above (Example 2 2)—FIG. 7) was digested with the enzymes XhoI and SalI and the large fragment, hereafter called fragment E, was isolated. This large fragment comprises the sequences of the URA3 gene, the origin of replication and the locus STB of the 2μ fragment, the ampicillin resistance gene Amp$^R$, the origin of replication of plasmid pBR322 and the UAS of the promoter of the GAL7 gene of S. cerevisiae, as well as the terminator of the PGK gene.

A double-stranded oligonucleotide sequence of about 400 base pairs, called fragment F, was synthesized in the form of an XhoI-SalI fragment. This sequence brings the TATA region and the initiation region of the ADH$_2$ promoter, which is extended by a synthetic sequence preceding the start of the pre-pro region Of the alpha pheromone. The sequence of this pre-pro region of the alpha pheromone differs from that described by Kurjan and Herskowitz, 1982, Cell, 30, 933–943, in the introduction of a HindIII site by the silent mutation of the TCT codon—corresponding to serine 81 of the precursor of the pheromone—to AGC. The whole sequence of the fragment is given below (SEQ ID NO: 27):

```
 XhoI
|TCGAGATACTCTTACTACTGCTCTCTTGTTGTTTTTATCACTTCTTGTTTC
-+--|--------+---------+---------+---------+---------
    |TATGAGAATGATGACGAGAGAACAACAAAAATAGTGAAGAACAAAG

TTCTTGGTAAATAGAATATCAAGCTACAAAAAGCATACAATCAACTATCAATCAGATCTA
----------+---------+---------+---------+---------+---------
AAGAACCATTTATCTTATAGTTCGATGTTTTTCGTATGTTAGTTGATAGTTAGTCTAGAT

ATATTAATAAAAAATGAGATTTCCTTCAATTTTTACTGCAGTTTTATTCGCAGCATCCTC
+---------+---------+---------+---------+---------+---------
TATAATTATTTTTTACTCTAAAGGAAGTTAAAAATGACGTCAAAATAAGCGTCGTAGGAG

CGCATTAGCTGCTCCAGTCAACACTACAACAGAAGATGAAACGGCACAAATTCCGGCTGA
```

-continued

```
+ .......... + .......... + .......... + .......... + .......... + .......... 
GCGTAATCGACGAGGTCAGTTGTGATGTTGTCTTCTACTTTGCCGTGTTTAAGGCCGACT

AGCTGTCATCGGTTACTTAGATTTAGAAGGGGATTTCGATGTTGCTGTTTTGCCATTTTC
+ .......... + .......... + .......... + .......... + .......... + .......... 
TCGACAGTAGCCAATGAATCTAAATCTTCCCCTAAAGCTACAACGACAAAACGGTAAAAG

CAACAGCACAAATAACGGGTTATTGTTTATAAATACTACTATTGCCAGCATTGCTGCTAA
+ .......... + .......... + .......... + .......... + .......... + .......... 
GTTGTCGTGTTTATTGCCCAATAACAAATATTTATGATGATAACGGTCGTAACGACGATT
```

```
                              H
                              i
                              n
                              d                          S
                              I                          a
                              I                          l
                              I                          I
AGAAGAAGGGGTAAGCTTGCATGCCTGCAGG
+ .......... + .......... + .......... + .......... + .......... 
TCTTCTTCCCCATTCGAACGTACGGACGTCCAGCT
```

Fragments E and F were ligated to give plasmid pEMR530 shown in FIG. 10, in which the symbols have the same meanings as in FIG. 7, the novel XhoI-SalI fragment (fragment F) introduced being represented by:⎯.

This plasmid comprises the artificial promoter of the invention, the sequence of which was given in Example 2.

2) Construction of plasmid pEMR583 (expression plasmid for the human cytokinin gro-β)

Hind III

```
AGCTTGGATAAAAGAGCGCCTTTGGCTACTGAATTGAGATGTCAATGTTTGCAAACCTTGCAAGG
    ACCTATTTTCTCGCGGAAACCGATGACTTAACTCTACAGTTACAAACGTTTGGAACGTTCCTTAA
```
EcoRI

Plasmid pEMR530 was completely digested with the enzymes NheI and HindIII. The small NheI-HindIII fragment, containing the artificial promoter and the pre-pro region of the a pheromone, as well as the URA3 gene, was purified (hereafter called fragment Plasmid pEMR473 was completely digested with the restriction enzymes NheI and BamHI. The large fragment (hereafter called fragment H), comprising the origin of replication and the locus STB of the 2μ fragment, the LEU2d gene, the ampicillin resistance gene, the origin of pBR322 and the terminator of the PGK gene, was purified.

The cDNA of gro-β was cloned and sequenced according to the method described by Tekamp-Olson et al., op. cit. The sequence of the cDNA of gro-β (described in detail in said reference—in particular FIG. 2) has an EcoRI site (Sequence: 5'-GAATTC) which covers the ATT codon (isoleucine in position +18 of the mature sequence of gro-β, Tekamp-Olson et al., op. cit.) and overlaps the two flanking codons GGA and CAC. The cloned cDNA of gro-β terminates at the 3' end in a polyA tail flanked by a BamHI restriction site.

The ECORI-BamHI fragment, comprising the major part of the coding sequence of gro-β, followed by the 3' sequence corresponding to the non-translated end of the mRNA flanked by the polyadenylated tail, was isolated by the customary techniques described in Maniatis et al. (op. cit.). The fragment is hereafter called fragment I.

A synthetic HindIII-EcoRI fragment, containing the end of the pre-pro region of the α pheromone (corresponding to the residues Set Leu Asp Lys Arg) and the start of the sequence coding for the mature protein of gro-β, was also prepared. The sequence of this fragment, called fragment J, is given below (SEQ ID NO: 28). It will be noted that the sequence corresponding to the start of the cDNA of gro-β has been modified relative to the sequence of the cDNA described by Tekamp-Olson et al., op. cit., so that the codons used are among those most frequently used by S. cerevisae (q.v. Sharp et al., 1986, Nucleic Acids. Research, vol. 14, 13, 5125–5143).

Fragments G, H, I and J were ligated to give plasmid pEMR583 shown in FIG. 11, in which the symbols have the same meanings as in FIGS. 7 and 10, fragment E being represented by ⎯ and fragment F by ■.

The nucleotide and peptide sequences of the start of the mature protein of gro-β, and of the end of the pre-pro region of the α pheromone, are as follows: (SEQ ID NO: 29 & 30)

| G T A.A G C.T T G.G A T.A A A.A G A. | G C G.C C T.T T G. |
|---|---|
| Val. Ser. Leu. Asp. Lys. Arg. | Ala. Pro. Leu. |
| End of the pre-pro region of the α pheromone | Start of the mature protein |

Cleavage site of the endopeptidase of cathepsin B type: yscF (product of the KEX2 gene)

EXAMPLE 9

Secretion of the cytokinin gro-β by yeast

1. Transformation of the EMY761 yeast strain by plasmid pEMR583 and expression of gro-β by the transformed strain. The EMY761 strain (Matα, leu2, ura3, his3) described in Example 3 was transformed by plasmid pEMR583 for the prototrophy of leucine by the technique already described in Example 3). Two transformed strains, hereafter called EMY761 pEMR583 (1) and EMY761 pEMR 583 (2), were retained.

2. Expression, in an Erlenmeyer flask, of the cDNA of gro-β by the EMY761 pEMR583 (1) and EMY761 pEMR583 (2) strains. Detection of the protein in the culture medium on polyacrylamide gel/sodium dodecylsulfate (SDS) according to the protocol described by LAEMMLI (U. K. LAEMMLI, Nature, 227 [1970] 680–685).

a. A colony of each of the EMY761 pEMR583 (1) and EMY761 pEMR583 (2) strains was cultured in 50 ml of uracil-free liquid medium. This medium contains the following per liter:
    6.7 g of Yeast Nitrogen base without amino acids (from DIFCO)
    5.0 g of casein hydrolyzate (Casamino acids from DIFCO)
    10 g of glucose.
After one night at 30° C., with agitation, the two cultures were centrifuged for 10 min at 7000 rpm. The residues were taken up in 10 ml of sterile distilled water and centrifuged again for 10 min at 7000 rpm. Expression of gro-β was induced by taking up the cells in 50 ml of ethanol-glycerol-galactose YNB medium. The ethanol-glycerol-galactose YNB medium contains the following per liter:
    6.7 g of Yeast Nitrogen base without Amino acids (from DIFCO)
    5.0 g of casein hydrolyzate (casamino acids from DIFCO)
    30 g of glycerol
    30 g of galactose
    10 ml of ethanol
The cultures were incubated again at 30° C. for 24 h, with agitation.

b. Control strain:
    The non-transformed EMY761 strain, i.e. the EMY761 strain without plasmid, was cultivated as above. It was subjected on the one hand to preculture in 50 ml of uracil-free liquid medium to which uracil had been added (20 μg/ml), and on the other hand to induction in 50 ml of ethanol-glycerol-galactose YNB medium to which uracil had been added (20 μg/ml).

Preparation of the samples:

The cells cultivated in 1 a/ and 1 b/ were centrifuged for 20 min at 10,000 rpm and the supernatant was collected. 5 ml of 50% trichloroacetic acid containing 2 mg/ml of deoxycholate were added to 10 ml of supernatant. The mixture was cooled at +4° C. for 30 min and then centrifuged for 30 min at 10,000 rpm. The residue was taken up in about 1 ml of cold acetone (+4° C.) and centrifuged again for 30 min at 10,000 rpm. After having been dried, the residue is taken up in about 20 μl of a so-called loading buffer consisting of Tris-HCl 0.125M pH 6.8, SDS 4%, bromophenol blue 0.002%, glycerol 20%, β-mercaptoethanol 10% (according to the protocol described by LAEMMLI [1970]). The residue is solubilized by boiling for 15 min and then neutralized by the addition of 10N sodium hydroxide solution until the bromophenol blue turns blue.

The samples are deposited on polyacrylamide gel/SDS:

| | |
|---|---|
| 1/ Size marker | |
| 2/ Non-induced non-transformed EMY761 | 20 μl deposited |
| 3/ Non-induced EMY761 pEMR583 (1) | 20 μl deposited |
| 4/ EMY761 pEMR583 (1) induced for 24 h | 15 μl deposited |
| 5/ EMY761 pEMR583 (1) induced for 24 h | 5 μl deposited |
| 6/ Size marker | |
| 7/ EMY761 pEMR583 (2) induced for 24 h | 5 μl deposited |
| 8/ EMY761 pEMR583 (2) induced for 24 h | 15 μl deposited |
| 9/ Non-induced EMY761 pEMR583 (2) | 20 μl |
| 10/ Induced non-transformed EMY761 | 20 μl deposited |

After electrophoresis, the proteins are stained with Coomassie blue.

RESULTS:

Analysis of the gel obtained shows that a supernumerary protein with an apparent molecular weight of about 8 kDa is produced by the EMY761 pEMR583 (1) strain (lanes 4 and 5) and EMY761 pEMR583 (2) strain (lanes 7 and 8) and is not produced in the culture supernatants of the non-transformed EMY761 strain (lanes 2 and 10). It is also apparent that the synthesis of this supernumerary protein is associated with induction of the promoter by growth on ethanol-glycerol-galactose (bands absent in lanes 3 and 9).

Analysis of the amino-terminal sequence of this protein purified by HPLC made it possible to verify that it was the mature gro-β protein described by Tekamp-Olson et al., op. cit.

It is therefore apparent that the cytokinin gro-β can be secreted under the control of the promoter of the invention.

The EMY761 pEMR583 (1) strain has been deposited at the Institut Pasteur under the number I-1021.

EXAMPLE 10

Construction of a vector for the expression and secretion of IL-8 in yeast: plasmid pEMR611 carrying the artificial promoter of the invention A second example of a secreted protein whose expression can be regulated by the promoter of the invention is the human cytokinin IL-8. This cytokinin of about 8000 Da, produced by monocytes, has been described by several teams: Yoshimura et al. (1987), J. Immunol., 139, 788–793, Shröder et al. (1987), J. Immunol., 139, 3474–3483, and Walz et al. (1987), Biochem-Biophys. Res. Commun., 149, 755–761. IL-8 acts as a chemical attractant of neutrophils. IL-8 has remarkable structural similarities with β-thromboglobin (Van Damme et al. (1989), Eur. J. Biochem. 181, 337–344). The cytokinin IL-8 exists in several forms which differ from one another in their NH$_2$-terminal end. The major form is composed of 72 amino acids but 5 other minor forms are also produced, 3 of which have a truncated NH$_2$-terminal end compared with the major form, and 2 which have respective extensions of 5 and 1 amino acids compared with this major form.

The cDNA of IL-8 was cloned and sequenced according to the method described by Matsushima et al., 1988, J. Exp. Med. 167, 1883–1993. The sequence of this cDNA contains a single HindIII site (5'-AAGCTT) which covers the 42nd and 43rd codons of the mature part (form 72 aa: q.v. Matsusnima et al., op. cit.).

Furthermore, the clone of the cDNA of IL-8 used in this cloning has a single BamHI site directly flanking the end (3') of the polyA tail. The BamHI-HindIII fragment, carrying the 3' end of the cDNA of IL-8, was purified.

A cloning vector was prepared in the following manner:

Plasmid pEMR583, described in Example 8, was digested with HindIII and BamHI.

This double digestion releases 5 fragments: the heaviest fragment, HindIII-BamHI, corresponds to the Cloning vector (about 7760 base pairs). The other 4, HindIII-HindIII (with sizes of 169 base pairs, 92 base pairs, 529 base pairs and 187 base pairs), correspond to the sequence of the cDNA of gro-$\beta$. The HindIII site of the cloning vector is located slightly upstream from the insertion site at the end of the pro sequence of the alpha pheromone (and covers the sequence of the codon—serine 81—of the precursor). The BamHI site is located upstream from the terminator of the PGK.

The DNA of the HindIII-BamHI fragment was purified. The HindIII-BamHI fragment, containing the 3' part of the sequence of the cDNA, was ligated with a synthetic HindIII-HindIII DNA fragment. The sequence of this fragment, which is given below, is intended for reconstituting the sequence of the major mature form of IL-8 (72 amino acids), preceded by the sequence of the Cleavage site (Ser-Leu-Asp-Lys-Arg). The novel HindIII-BamHI fragment was ligated with the HindIII-BamHI fragment corresponding to the cloning vector. The sequence of the synthetic HindIII-HindIII fragment is as follows (SEQ ID NO: 31):

```
5'-AGCTTGGATAAAAGATCTGCTAAGGAATTGAGATGTCAATGTATCAAGACTTACTCTAAGCCATTCC
   ACCTATTTTCTAGACGATTCCTTAACTCTACAGTTACATAGTTCTGAATGAGATTCGGTAAGG

ACCCAAAGTTCATCAAGGAATTGAGAGTTATCGAATCTGGTCCACACTGTGCTAACACTGAAATTAT
TGGGTTTCAAGTAGTTCCTTAACTCTCAATAGCTTAGACCAGGTGTGACACGATTGTGACTTTAATA

CGTTA
GCAATTCGA-5'
```

The plasmid obtained in this way, carrying the cDNA of IL-8 preceded by the pre-pro sequence of the $\alpha$ pheromone and the promoter of the invention, whose sequence was specified in Example 2, is called pEMR611.

EXAMPLE 11

Transformation of the EMY761 yeast strain by plasmid pEMR611. and secretion of IL-8

The EMY761 Strain (Mat$\alpha$, ura3, leu2, his3), described in Example 3, was transformed into the (leu+) strain by the DNA of plasmid pEMR611 according to the technique already described. Of the (leu+) colonies obtained, one was removed at random and cultivated in order to study the secretion of IL-8. This strain is hereafter called EMY761 pEMR611.

The protocol for analysis of the proteins secreted by the yeast is that described in Example 9. The proteins secreted by EMY761 pEMR611 were compared with those secreted by EMY761. This revealed a supernumerary major band corresponding to a protein of 8000 Da secreted by the EMY761 pEMR611 cells induced by galactose. This protein is specifically recognized by rabbit antibodies directed against human IL-8 (supplied by Endogen: Anti human IL-8 polyvalent P801) according to the results of analysis by Western blot—a method which is well known to those skilled in the art and whose protocol is given in detail in Example 4.

Expression plasmid pEMR611 therefore permits a high level of expression of IL-8 in transformed yeasts. This expression is under the control of the artificial promoter of the invention.

The EMY761 pEMR611 strain has been deposited in the Institut Pasteur collection under the number I-1023.

EXAMPLE 12

Construction of a vector for the expression and secretion of hirudin: plasmid pEMR576 carrying the artificial promoter of the invention Naturally produced by the Hirudo leech, hirudin is a very specific and very effective inhibitor of thrombin. A number of variants have been identified and designated by $HV_1$, $HV_2$ and $HV_3$ (Dodt J. et al. (1986), FEBS Lett. 202, 373, 377). Some of these natural variants and other analogs have subsequently been prepared by genetic engineering in a variety of host cells. The present Example concerns the variant rHV$_2$-Lys47 described in the patent publication EP-A-0273800. More particularly, the expressed sequence codes for a precursor of this variant rHV$_2$-Lys47, which contains a signal sequence: Met-Arg-Phe-Ser-Thr-Thr-Val-Ala-Thr-Ala-Ala-Tyr-Ala-Leu-Phe-Phe-Thr-Ala-Ser-Gln-Val-Ser-Ala, directly preceding the start of the sequence of mature hirudin.

The construction and the structure of this precursor are described in the patent publication FR 2646437. The expression of this precursor permits the release of the variant rHV$_2$-Lys47 in the culture supernatant of the transformed cells.

Plasmid pTG3867, whose construction and description are given in detail in the patent application FR 2 646 437, is a secretion vector for hirudin. In this construction, the hirudin is synthesized in the form of a precursor containing a signal sequence. The hirudin is placed behind the promoter of the MF$\alpha$1 gene, which is a constitutive promoter in yeast strains of the $\alpha$ conjugation type.

Construction of plasmid pEMR547

Plasmid pEMR547 is derived from plasmid pEMR515 (cf. Example 2) by deletion of the small sequence originating from plasmid 2$\mu$ and located between the end of the LEU2d gene and the EcORI site bordering the sequence of plasmid pBR322. Plasmid pEMR515 was digested partially with BspMI and totally with EcoRI. The large BspMI-EcORI fragment, corresponding to plasmid pEMR515 from which the 3' part of LEU2 and the small adjoining sequence of the 2$\mu$ fragment have been deleted, was ligated with a synthetic BspMI-EcoRI° sequence intended for reconstituting the 3' region of the LEU2d gene.

This synthetic sequence is as follows (SEQ ID NO: 32):

EcoRI°

-continued
```
AATTGCCCGGGACGTCTTATGTACAAATATCATAAAAAAAGAGAATCTTTT
+---------+---------+---------+---------+---------+---------
    CGGGCCCTGCAGAATACATGTTTATAGTATTTTTTCTCTTAGAAAAA AAGCAAGGATTTTCTTAACTTCTTCGGCGACAGCATCACCGACTTCGGTGGTACTGTTGG
+---------+---------+---------+---------+---------+---------
TTCGTTCCTAAAAGAATTGAAGAAGCCGCTGTCGTAGTGGCTGAAGCCACCATGACAACC B
                                                           s
                                                           P
                                                           M
                                                           I
AACCACCTAAATCACCAGTTCTGATACCTGCATCC
+---------+---------+---------+--------
TTGGTGGATTTAGTGGTCAAGACTATGGACGTAGGTTTT
```

The reconstituted plasmid is called pEMR547.

Construction of plasmid pEMR568

Plasmid pEMR568 is derived from pEMR547 in the following manner:

The DNA of plasmid pEMR547 was digested with MluI and NheI. This double digestion makes it possible to linearize plasmid pEMR547 (6.6 kb), the 2 sites MluI and NheI being situated within a few base pairs of one another. A double-stranded synthetic oligonucleotide of the sequence (SEQ ID NO: 33)

```
CTAGCGAGCTCAAGCTTA
    GCTCGAGTTCGAATGCGC
``` was inserted between these 2 sites.

The resulting plasmid is called pEMR568.

Construction of plasmid pEMR576, an expression plasmid for hirudin

The sequence of the variant rHV2-Lys47 of hirudin was obtained from plasmid pTG3867, whose construction and description are given in detail in the patent application FR 2 646 437. In this construction, the hirudin is synthesized in the form of a precursor composed of a signal peptide of 23 amino acids (including the methionine corresponding to the initiation codon). The messenger RNA coding for the precursor is transcribed with the aid of the MFα1 promoter, which is a constitutive promoter in yeast strains of the alpha conjugation type.

AccI-SalI double digestion of plasmid pTG3867 releases several fragments, the shortest of which, numbering about 200 base pairs, is readily purifiable on 2% agarose gel. The AccI site which borders this fragment is located a few base pairs from the start of the mature sequence (SEQ ID NO: 34), according to the sequence

```
           AccI
    ATTACG | TATACAGAC...
          |
          ‾‾‾‾‾‾|
      TAATGC AT | ATGTCTG
               Mature
               sequence
```

The SalI site is located downstream from the stop codon of the coding sequence of hirudin.

The AccI-SalI fragment of 200 base pairs carries the information for the greater part of the mature sequence of hirudin. The complementary information (signal sequence and start of the mature sequence) is provided by a synthetic sequence of about 90 nucleotides, which is specified below (SEQ ID NO: 35):

```
CGATATACACAATGCGTTTCTCTACTACAGTCGCTACTGCAGCTACTGCGCTATTTTTCACAGCCTCC
    TATATGTGTTACGCAAAGAGATGATGTCAGCGATGACGTCGATGACGCGATAAAAAGTGTCGGAGG

CCAAGTTTCAGCTATTACGT
GGTTCAAAGTCGATAATGCATA
```

Vector pEMR468 was linearized with SalI and partially digested with ClaI, The ClaI-SalI fragment of about 5.6 kb, corresponding to this vector from which the sequence of urate oxidase has been deleted, was ligated with the AccI-SalI fragment of about 200 base pairs, which carries the information for the sequence of mature hirudin, and with the small synthetic ClaI-AccI sequence intended for reconstituting the sequence of the precursor of hirudin. The resulting plasmid is called pEMR576.

EXAMPLE 13

Secretion of hirudin

1) Transformation of the EMY761 strain by plasmid pEMR576

The EMY761 strain (Matα, ura3, his3, leu2) was transformed into the (leu+) strain by plasmid pEMR576 according to the technique already described.

A transformed strain, hereafter called EMY761 pEMR576, was isolated.

2) Expression of hirudin

As a negative control, a (leu+) strain derived from EMY761, hereafter called EMY761 (leu+), was constructed. The technique used is described in detail in the patent application FR 2 646 437. The EMY761 pEMR576 and EMY761 (leu+) strains were cultivated in parallel in the manner described below:

The precultures take place in medium of the following composition: Yeast Nitrogen Base (Difco) 0.7%, histidine 50 μg/ml and uracil 50 μg/ml. After 24 h, the cultures are inoculated with $10^5$ cells in medium having the following composition: Yeast Nitrogen Base (Difco) 0.7%, ethanol 1%, casamino acids 0.5%, uracil 100 μg/ml, glycerol 3% and galactose 1%. After culture for 72 h in the latter medium, the supernatant is separated from the cells by filtration on 0.2μ. The inhibitory activity of the supernatant on thrombin is measured by using the colorimetric test described in FR 2 646 437 (proteolytic activity of thrombin on a synthetic substrate: chromozyme TH marketed by Boehringer Mannheim).

The Table below shows the results of the assays in μg of hirudin per ml of supernatant, at an optical density of 1, i.e. $0.3 \times 10^7$ cells/ml.

| Strain | μg/ml |
|---|---|
| EMY761 (leu⁻) | non-detectable |
| EMY761 pEMR576 | 0.5 |

It is therefore apparent that hirudin can be secreted under the control of the promoter of the invention.

The EMY761 pEMR576 strain has been deposited in the CNCM under the number I-1022.

---

What is claimed is:

1. An artificial promoter for the expression of proteins in yeast, which comprises the following sequence (SEQ ID NO. 3):

```
M
l
u
I
CGCGTCTATACTTCGGAGCACTGTTGAG
     AGATATGAAGCCTCGTGACAACTC

CCAAGGCTCATTAGATATATTTTCTGTCAT
     GCTTCCGAGTAATCTATATAAAAGACAGTA

TTTCCTTAACCCAAAAATAAGGGAGAGGGT
AAAGGAATTGGGTTTTTATTCCCTCTCCCA

CCAAAAAGCGCTCGGACAACTGTTGACCGT
     GGTTTTTCGCGAGCCTGTTGACAACTGGCA

GATCCGAAGGACTGGCTATACAGTGTTCAC
CTAGGCTTCCTGACCGATATGTCACAAGTG

AAAATAGCCAAGCTGAAAATAATGTGTAGC
     TTTTATCGGTTCGACTTTTATTACACATCG

S
                                p
                                h
                                I
CTTTAGCTATGTTCAGTTAGTTTGGCATGC
GAAATCGATACAAGTCAATCAAACCGTACG

CTATCACATATAAATAGA
          GATAGTGTATATTTATCT

GTGCCAGTAGCGACTTTTTTCACACTCGAG
CACGGTCATCGCTGAAAAAAGTGTGAGCTC

ATACTCTTACTACTGCTCTCTTGTTGTTTT
     TATGAGAATGATGACGAGAGAACAACAAAA

TATCACTTCTTGTTTCTTCTTCGTAAATAG
ATAGTGAAGAACAAAGAAGAACCATTTATC

AATATCAAGCTACAAAAAGCATACAATCAA
     TTATAGTTCGATGTTTTTCGTATGTTAGTT
                                    C
                                    l
                                    a
                                    I
     CTATCAACTATTAACTATAT
     GATAGTTGATAATTGATATAGC.
```

2. An expression vector for yeast comprising a gene of interest, the transcription of which is controlled by the promoter according to claim 1.

3. An expression vector according to claim 2, wherein the gene of interest is a gene coding for a protein which is toxic to yeast.

4. An expression vector according to claim 2, wherein the gene of interest is a gene coding for urate oxidase.

5. A strain of yeast which is transformed by an expression vector according to claim 3.

6. A strain of yeast which is transformed by an expression vector according to claim 4.

7. A strain of *Saccharomyces cerevisiae* which is transformed by an expression vector according to claim 3.

8. A strain of *Saccharomyces cerevisiae* which is transformed by an expression vector according to claim 4.

* * * * *

UNITED STATES PATENT AND TRADEMARK OFFICE
CERTIFICATE OF CORRECTION

| | | |
|---|---|---|
| PATENT NO. | : | 5,407,822 |
| DATED | : | April 18, 1995 |
| INVENTOR(S) | : | Pascal LEPLATOIS, et. al |

It is certified that error appears in the above-identified patent and that said Letters Patent is hereby corrected as shown below:

On the title page; Priority Application Data was omitted, please insert --France FR89 17467 filed on December 29, 1989; PCT/FR90/00957 filed on December 28, 1990--.

Signed and Sealed this

Twenty-fourth Day of August, 1999

Attest:

Q. TODD DICKINSON

*Attesting Officer*          *Acting Commissioner of Patents and Trademarks*

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 207 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Saccharomyces cerevisiae ( v i i ) IMMEDIATE SOURCE:
        ( B ) CLONE: sub-sequence upstream of TATA signal promoting gene GAL7

( i x ) FEATURE:
        ( A ) NAME/KEY: misc_binding
        ( B ) LOCATION: 1..4
        ( D ) OTHER INFORMATION: /standard_name="site MluI"

( i x ) FEATURE:
        ( A ) NAME/KEY: misc_binding
        ( B ) LOCATION: 204..207
        ( D ) OTHER INFORMATION: /standard_name="site SphI"

( i x ) FEATURE:
        ( A ) NAME/KEY: misc_signal
        ( B ) LOCATION: 11..33
        ( D ) OTHER INFORMATION: /function="upstream activation sequence (UAS) no.1"

( i x ) FEATURE:
        ( A ) NAME/KEY: misc_signal
        ( B ) LOCATION: 98..120
        ( D ) OTHER INFORMATION: /function="UAS no.2"

( x i ) SEQUENCE DESCRIPTION: SEQ ID NO:1:

```
CGCGTCTATA  CTTCGGAGCA  CTGTTGAGCG  AAGGCTCATT  AGATATATTT  TCTGTCATTT      60

TCCTTAACCC  AAAAATAAGG  GAGAGGGTCC  AAAAAGCGCT  CGGACAACTG  TTGACCGTGA     120

TCCGAAGGAC  TGGCTATACA  GTGTTCACAA  AATAGCCAAG  CTGAAAATAA  TGTGTAGCCT     180

TTAGCTATGT  TCAGTTAGTT  TGGCATG                                           207
```

( 2 ) INFORMATION FOR SEQ ID NO:2:

( i ) SEQUENCE CHARACTERISTICS:
        ( A ) LENGTH: 159 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: sub-sequence of the sequence of an ADH2 promoter...

( i x ) FEATURE:
    ( A ) NAME/KEY: misc_binding
    ( B ) LOCATION: 159
    ( D ) OTHER INFORMATION: /standard_name="site ClaI"

( x i ) SEQUENCE DESCRIPTION: SEQ ID NO:2:

| | | | | | |
|---|---|---|---|---|---|
| CCTATCACAT | ATAAATAGAG | TGCCAGTAGC | GACTTTTTC | ACACTCGAGA | TACTCTTACT | 60
| ACTGCTCTCT | TGTTGTTTT | ATCACTTCTT | GTTTCTTCTT | GGTAAATAGA | ATATCAAGCT | 120
| ACAAAAAGCA | TACAATCAAC | TATCAACTAT | TAACTATAT | | | 159

( 2 ) INFORMATION FOR SEQ ID NO:3:

( i ) SEQUENCE CHARACTERISTICS:
        ( A ) LENGTH: 366 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: artificial promoter for the expression of
              proteins in yeast ( i x ) FEATURE:
        ( A ) NAME/KEY: misc_binding
        ( B ) LOCATION: 1..4
        ( D ) OTHER INFORMATION: /standard_name="site MluI"

( i x ) FEATURE:
        ( A ) NAME/KEY: misc_binding
        ( B ) LOCATION: 207
        ( D ) OTHER INFORMATION: /standard_name="site SphI"

( i x ) FEATURE:
        ( A ) NAME/KEY: misc_binding
        ( B ) LOCATION: 366
        ( D ) OTHER INFORMATION: /standard_name="site ClaI"

( x i ) SEQUENCE DESCRIPTION: SEQ ID NO:3:

| | | | | | |
|---|---|---|---|---|---|
| CGCGTCTATA | CTTCGGAGCA | CTGTTGAGCG | AAGGCTCATT | AGATATATTT | TCTGTCATTT | 60
| TCCTTAACCC | AAAAATAAGG | GAGAGGGTCC | AAAAAGCGCT | CGGACAACTG | TTGACCGTGA | 120
| TCCGAAGGAC | TGGCTATACA | GTGTTCACAA | AATAGCCAAG | CTGAAAATAA | TGTGTAGCCT | 180
| TTAGCTATGT | TCAGTTAGTT | TGGCATGCCT | ATCACATATA | AATAGAGTGC | CAGTAGCGAC | 240
| TTTTTCACA | CTCGAGATAC | TCTTACTACT | GCTCTCTTGT | TGTTTTATC | ACTTCTTGTT | 300
| TCTTCTTGGT | AAATAGAATA | TCAAGCTACA | AAAAGCATAC | AATCAACTAT | CAACTATTAA | 360
| CTATAT | | | | | | 366

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: oligonucleotide;primer of reverse
              transcription ( x i ) SEQUENCE DESCRIPTION: SEQ ID NO:4:

GATCCGGGCC CT                                                                12

( 2 ) INFORMATION FOR SEQ ID NO:5:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( v i i ) IMMEDIATE SOURCE:
    ( B ) CLONE: hydrolysis product T17

( x i ) SEQUENCE DESCRIPTION: SEQ ID NO:5:

```
Asn  Val  Gln  Val  Asp  Val  Val  Glu  Gly  Lys
1                  5                        10
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T20

( x i ) SEQUENCE DESCRIPTION: SEQ ID NO:6:

```
Asn  Phe  Ser  Gly  Leu  Gln  Glu  Val
1                  5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T23

( x i ) SEQUENCE DESCRIPTION: SEQ ID NO:7:

```
Phe  Asp  Ala  Thr  Trp  Ala
1                  5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T27

( x i ) SEQUENCE DESCRIPTION: SEQ ID NO:8:

```
His  Tyr  Phe  Glu  Ile  Asp  Leu  Ser
1                  5
```

( 2 ) INFORMATION FOR SEQ ID NO:9:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T28

( x i ) SEQUENCE DESCRIPTION: SEQ ID NO:9:

Ile Leu Ser Thr Asp Val Asp Ala Thr Trp Gln Trp Lys
1               5                   10

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T29

( x i ) SEQUENCE DESCRIPTION: SEQ ID NO:10:

His Tyr Phe Glu Ile Asp Leu Ser Trp His Lys
1               5                   10

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T31

( x i ) SEQUENCE DESCRIPTION: SEQ ID NO:11:

Ser Thr Asn Ser Gln Phe Trp Gly Phe Leu Arg
1               5                   10

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T32

( x i ) SEQUENCE DESCRIPTION: SEQ ID NO:12:

Gln Asn Pro Val Thr Pro Pro Glu Leu Phe Gly Ser Ile Leu Gly Thr
1               5                   10                  15

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: hydrolysis product T33

( x i ) SEQUENCE DESCRIPTION: SEQ ID NO:13:

Gln Asn Pro Val Thr Pro Pro Glu Leu Phe Gly Ser Ile Leu Gly Thr
1               5                   10                  15

( 2 ) INFORMATION FOR SEQ ID NO:14:

( i ) SEQUENCE CHARACTERISTICS:
        ( A ) LENGTH: 17 amino acids (B) TYPE: amino acid
(D) TOPOLOGY: linear (ii) MOLECULE TYPE: peptide (vii) IMMEDIATE SOURCE:
(B) CLONE: hydrolysis product V1

(xi) SEQUENCE DESCRIPTION: SEQ ID NO:14:

Tyr Ser Leu Pro Asn Lys His Tyr Phe Glu Ile Asp Leu Ser Trp His
1               5                   10                  15

Lys (2) INFORMATION FOR SEQ ID NO:15:

(i) SEQUENCE CHARACTERISTICS:
(A) LENGTH: 16 amino acids
(B) TYPE: amino acid
(D) TOPOLOGY: linear (ii) MOLECULE TYPE: peptide (vii) IMMEDIATE SOURCE:
(B) CLONE: hydrolysis product V2

(xi) SEQUENCE DESCRIPTION: SEQ ID NO:15:

Val Thr Leu Lys Thr Phe Ala Glu Asp Asn Ser Ala Ser Val Gln Ala
1               5                   10                  15

(2) INFORMATION FOR SEQ ID NO:16:

(i) SEQUENCE CHARACTERISTICS:
(A) LENGTH: 24 amino acids
(B) TYPE: amino acid
(D) TOPOLOGY: linear (ii) MOLECULE TYPE: peptide (vii) IMMEDIATE SOURCE:
(B) CLONE: hydrolysis product V3

(xi) SEQUENCE DESCRIPTION: SEQ ID NO:16:

Thr Ser Tyr Thr Lys Ala Asp Asn Ser Val Ile Val Ala Thr Asp Ser
1               5                   10                  15

Ile Lys Asn Thr Ile Tyr Ile Thr
                20

(2) INFORMATION FOR SEQ ID NO:17:

(i) SEQUENCE CHARACTERISTICS:
(A) LENGTH: 28 amino acids
(B) TYPE: amino acid
(D) TOPOLOGY: linear (ii) MOLECULE TYPE: peptide (vii) IMMEDIATE SOURCE:
(B) CLONE: hydrolysis product V5

(xi) SEQUENCE DESCRIPTION: SEQ ID NO:17:

Gly Lys Gly Ile Asp Ile Lys Ser Ser Leu Ser Gly Leu Thr Val Leu
1               5                   10                  15

Lys Ser Thr Asn Ser Gln Phe Trp Gly Phe Leu Arg
                20                  25

(2) INFORMATION FOR SEQ ID NO:18:

(i) SEQUENCE CHARACTERISTICS:
(A) LENGTH: 17 amino acids
(B) TYPE: amino acid
(D) TOPOLOGY: linear ( i i ) MOLECULE TYPE: peptide ( v i i ) IMMEDIATE SOURCE:
( B ) CLONE: hydrolysis product V6

( x i ) SEQUENCE DESCRIPTION: SEQ ID NO:18:

Gly Lys Gly Ile Asp Ile Lys Ser Ser Leu Ser Gly Leu Thr Val Leu
1               5                   10                  15

Lys ( 2 ) INFORMATION FOR SEQ ID NO:19:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i i ) IMMEDIATE SOURCE:
( B ) CLONE: oligonucleotide;probe ( x i ) SEQUENCE DESCRIPTION: SEQ ID NO:19:

TCDATYTCRA ARTARTG                                                      17

( 2 ) INFORMATION FOR SEQ ID NO:20:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i i ) IMMEDIATE SOURCE:
( B ) CLONE: oligonucleotide;probe ( x i ) SEQUENCE DESCRIPTION: SEQ ID NO:20:

ARRAANCCCC ARAAYTG                                                      17

( 2 ) INFORMATION FOR SEQ ID NO:21:

( i ) SEQUENCE CHARACTERISTICS:
( A ) LENGTH: 360 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i i ) IMMEDIATE SOURCE:
( B ) CLONE: SmaI-BamHI fragment ( i x ) FEATURE:
( A ) NAME/KEY: misc_binding
( B ) LOCATION: 4
( D ) OTHER INFORMATION: /standard_name="site MluI"

( i x ) FEATURE:
( A ) NAME/KEY: misc_binding
( B ) LOCATION: 154
( D ) OTHER INFORMATION: /standard_name="site SphI"

( i x ) FEATURE:
( A ) NAME/KEY: misc_binding
( B ) LOCATION: 313

( D ) OTHER INFORMATION: /standard_name="site ClaI"

( i x ) FEATURE:
    ( A ) NAME/KEY: misc_binding
    ( B ) LOCATION: (343 344)
    ( D ) OTHER INFORMATION: /standard_name="site BamHI"

( x i ) SEQUENCE DESCRIPTION: SEQ ID NO:21:

| | | | | | | |
|---|---|---|---|---|---|---|
| GGGACGCGTC | TCCTCTGCCG | GAACACCGGG | CATCTCCAAC | TTATAAGTTG | GAGAAATAAG | 60 |
| AGAATTTCAG | ATTGAGAGAA | TGAAAAAAAA | AAAAAAAAAA | AAGGCAGAGG | AGAGCATAGA | 120 |
| AATGGGGTTC | ACTTTTGGT | AAAGCTATAG | CATGCCTATC | ACATATAAAT | AGAGTGCCAG | 180 |
| TAGCGACTTT | TTTCACACTC | GAGATACTCT | TACTACTGCT | CTCTTGTTGT | TTTTATCACT | 240 |
| TCTTGTTTCT | TCTTGGTAAA | TAGAATATCA | AGCTACAAAA | AGCATACAAT | CAACTATCAA | 300 |
| CTATTAACTA | TATCGATACC | ATATGGATCC | GTCGACTCTA | GAGGATCGTC | GACTCTAGAG | 360 |

( 2 ) INFORMATION FOR SEQ ID NO:22:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i i ) IMMEDIATE SOURCE:
        ( B ) CLONE: ClaI-AccI fragment ( i x ) FEATURE:
        ( A ) NAME/KEY: misc_binding
        ( B ) LOCATION: 58
        ( D ) OTHER INFORMATION: /standard_name="site AccI"

( x i ) SEQUENCE DESCRIPTION: SEQ ID NO:22:

| | | | | | | |
|---|---|---|---|---|---|---|
| CGATATACAC | AATGTCTGCT | GTTAAGGCTG | CTAGATACGG | TAAGGACAAC | GTTAGAGT | 58 |

( 2 ) INFORMATION FOR SEQ ID NO:23:

( i ) SEQUENCE CHARACTERISTICS:
        ( A ) LENGTH: 1013 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: AccI-BamHI fragment ( x i ) SEQUENCE DESCRIPTION: SEQ ID NO:23:

| | | | | | | |
|---|---|---|---|---|---|---|
| CTACAAGGTT | CACAAGGACG | AGAAGACCGG | TGTCCAGACG | GTGTACGAGA | TGACCGTCTG | 60 |
| TGTGCTTCTG | GAGGGTGAGA | TTGAGACCTC | TTACACCAAG | GCCGACAACA | GCGTCATTGT | 120 |
| CGCAACCGAC | TCCATTAAGA | ACACCATTTA | CATCACCGCC | AAGCAGAACC | CCGTTACTCC | 180 |
| TCCCGAGCTG | TTCGGCTCCA | TCCTGGGCAC | ACACTTCATT | GAGAAGTACA | ACCACATCCA | 240 |
| TGCCGCTCAC | GTCAACATTG | TCTGCCACCG | CTGGACCCGG | ATGGACATTG | ACGGCAAGCC | 300 |
| ACACCCTCAC | TCCTTCATCC | GCGACAGCGA | GGAGAAGCGG | AATGTGCAGG | TGGACGTGGT | 360 |
| CGAGGGCAAG | GGCATCGATA | TCAAGTCGTC | TCTGTCCGGC | CTGACCGTGC | TGAAGAGCAC | 420 |
| CAACTCGCAG | TTCTGGGGCT | TCCTGCGTGA | CGAGTACACC | ACACTTAAGG | AGACCTGGGA | 480 |
| CCGTATCCTG | AGCACCGACG | TCGATGCCAC | TTGGCAGTGG | AAGAATTTCA | GTGGACTCCA | 540 |
| GGAGGTCCGC | TCGCACGTGC | CTAAGTTCGA | TGCTACCTGG | GCCACTGCTC | GCGAGGTCAC | 600 |

-continued

| | | | | | | |
|---|---|---|---|---|---|---|
| TCTGAAGACT | TTTGCTGAAG | ATAACAGTGC | CAGCGTGCAG | GCCACTATGT | ACAAGATGGC | 660 |
| AGAGCAAATC | CTGGCGCGCC | AGCAGCTGAT | CGAGACTGTC | GAGTACTCGT | TGCCTAACAA | 720 |
| GCACTATTTC | GAAATCGACC | TGAGCTGGCA | CAAGGGCCTC | CAAAACACCG | GCAAGAACGC | 780 |
| CGAGGTCTTC | GCTCCTCAGT | CGGACCCCAA | CGGTCTGATC | AAGTGTACCG | TCGGCCGGTC | 840 |
| CTCTCTGAAG | TCTAAATTGT | AAACCAACAT | GATTCTCACG | TTCCGGAGTT | TCCAAGGCAA | 900 |
| ACTGTATATA | GTCTGGGATA | GGGTATAGCA | TTCATTCACT | TGTTTTTAC | TTCCAAAAAA | 960 |
| AAAAAAAAAA | AAAAAAAAAA | AAAAAAAAAA | AAAAAAAAAA | AAAAAGGGC | CCG | 1013 |

( 2 ) INFORMATION FOR SEQ ID NO:24:

( i ) SEQUENCE CHARACTERISTICS:
        ( A ) LENGTH: 309 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: ADH2 promoter similar to the natural ADH2
            promoter ( i x ) FEATURE:
        ( A ) NAME/KEY: misc_binding
        ( B ) LOCATION: 150
        ( D ) OTHER INFORMATION: /standard_name="site SphI"

( i x ) FEATURE:
        ( A ) NAME/KEY: misc_binding
        ( B ) LOCATION: 309
        ( D ) OTHER INFORMATION: /standard_name="site ClaI"

( i x ) FEATURE:
        ( A ) NAME/KEY: promoter
        ( B ) LOCATION: 259..270

( i x ) FEATURE:
        ( A ) NAME/KEY: TATA_signal
        ( B ) LOCATION: 160..163

( x i ) SEQUENCE DESCRIPTION: SEQ ID NO:24:

| | | | | | | |
|---|---|---|---|---|---|---|
| CGCGTCTCCT | CTGCCGGAAC | ACCGGGCATC | TCCAACTTAT | AAGTTGGAGA | AATAAGAGAA | 60 |
| TTTCAGATTG | AGAGAATGAA | AAAAAAAAA | AAAAAAAGG | CAGAGGAGAG | CATAGAAATG | 120 |
| GGGTTCACTT | TTTGGTAAAG | CTATAGCATG | CCTATCACAT | ATAAATAGAG | TGCCAGTAGC | 180 |
| GACTTTTTC | ACACTCGAGA | TACTCTTACT | ACTGCTCTCT | TGTTGTTTTT | ATCACTTCTT | 240 |
| GTTTCTTCTT | GGTAAATAGA | ATATCAAGCT | ACAAAAGCA | TACAATCAAC | TATCAACTAT | 300 |
| TAACTATAT | | | | | | 309 |

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: adapter containing MluI and modified XbaI
            sticky ends ( x i ) SEQUENCE DESCRIPTION: SEQ ID NO:25:

CTAGGCTAGC GGGCCCGCAT GCA                                                23

( 2 ) INFORMATION FOR SEQ ID NO:26:

( i ) SEQUENCE CHARACTERISTICS:
   ( A ) LENGTH: 63 base pairs
   ( B ) TYPE: nucleic acid
   ( C ) STRANDEDNESS: double
   ( D ) TOPOLOGY: linear ( i i ) MOLECULE TYPE: DNA (genomic)

( v i i ) IMMEDIATE SOURCE:
   ( B ) CLONE: EcoRI-BamHI fragment ( x i ) SEQUENCE DESCRIPTION: SEQ ID NO:26:

```
AATTTCAGCT GAGCGCCGGT CGCTACCATT ACCAGTTGGT CTGGTGTCAA AAATAATAAT      60

AAG                                                                    63
```

( 2 ) INFORMATION FOR SEQ ID NO:27:

( i ) SEQUENCE CHARACTERISTICS:
      ( A ) LENGTH: 382 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( v i i ) IMMEDIATE SOURCE:
      ( B ) CLONE: fragment F ( i x ) FEATURE:
      ( A ) NAME/KEY: misc_binding
      ( B ) LOCATION: 364
      ( D ) OTHER INFORMATION: /standard_name="site Hind III"

( i x ) FEATURE:
      ( A ) NAME/KEY: misc_binding
      ( B ) LOCATION: 382
      ( D ) OTHER INFORMATION: /standard_name="site SalI"

( x i ) SEQUENCE DESCRIPTION: SEQ ID NO:27:

```
TCGAGATACT CTTACTACTG CTCTCTTGTT GTTTTTATCA CTTCTTGTTT CTTCTTGGTA      60

AATAGAATAT CAAGCTACAA AAAGCATACA ATCAACTATC AATCAGATCT AATATTAATA     120

AAAAATGAGA TTTCCTTCAA TTTTTACTGC AGTTTTATTC GCAGCATCCT CCGCATTAGC     180

TGCTCCAGTC AACACTACAA CAGAAGATGA AACGGCACAA ATTCCGGCTG AAGCTGTCAT     240

CGGTTACTTA GATTTAGAAG GGGATTTCGA TGTTGCTGTT TTGCCATTTT CCAACAGCAC     300

AAATAACGGG TTATTGTTTA TAAATACTAC TATTGCCAGC ATTGCTGCTA AAGAAGAAGG     360

GGTAAGCTTG CATGCCTGCA GG                                              382
```

( 2 ) INFORMATION FOR SEQ ID NO:28:

( i ) SEQUENCE CHARACTERISTICS:
      ( A ) LENGTH: 65 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( v i i ) IMMEDIATE SOURCE:
      ( B ) CLONE: Hind III - EcoRI fragment ( x i ) SEQUENCE DESCRIPTION: SEQ ID NO:28:

```
AGCTTGGATA AAAGAGCGCC TTTGGCTACT GAATTGAGAT GTCAATGTTT GCAAACCTTG      60

CAAGG                                                                  65
```

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: mat_peptide
        (B) LOCATION: 19..27

(ix) FEATURE:
        (A) NAME/KEY: misc_structure
        (B) LOCATION: 1..27
        (D) OTHER INFORMATION: /function="nucleotides coding for transcripted protein"

(ix) FEATURE:
        (A) NAME/KEY: CDS
        (B) LOCATION: 1..27

(xi) SEQUENCE DESCRIPTION: SEQ ID NO:29:

```
GTA  AGC  TTG  GAT  AAA  AGA  GCG  CCT  TTG                         27
Val  Ser  Leu  Asp  Lys  Arg  Ala  Pro  Leu
-6   -5                                  1
```

(2) INFORMATION FOR SEQ ID NO:30:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:30:

```
Val  Ser  Leu  Asp  Lys  Arg  Ala  Pro  Leu
-6   -5                                  1
```

(2) INFORMATION FOR SEQ ID NO:31:

(i) SEQUENCE CHARACTERISTICS:
        (A) LENGTH: 139 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vii) IMMEDIATE SOURCE:
        (B) CLONE: Hind III - Hind III fragment (xi) SEQUENCE DESCRIPTION: SEQ ID NO:31:

```
AGCTTGGATA AAAGATCTGC TAAGGAATTG AGATGTCAAT GTATCAAGAC TTACTCTAAG      60
CCATTCCACC CAAAGTTCAT CAAGGAATTG AGAGTTATCG AATCTGGTCC ACACTGTGCT     120
AACACTGAAA TTATCGTTA                                                  139
```

(2) INFORMATION FOR SEQ ID NO:32:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: DNA (genomic)

( i i i ) HYPOTHETICAL: NO ( v i i ) IMMEDIATE SOURCE:
    ( B ) CLONE: EcoRI-BspMI fragment ( i x ) FEATURE:
    ( A ) NAME/KEY: misc_binding
    ( B ) LOCATION: 147
    ( D ) OTHER INFORMATION: /standard_name="site BspMI"

( x i ) SEQUENCE DESCRIPTION: SEQ ID NO:32:

```
AATTGCCCGG GACGTCTTAT GTACAAATAT CATAAAAAAA GAGAATCTTT TTAAGCAAGG      60
ATTTTCTTAA CTTCTTCGGC GACAGCATCA CCGACTTCGG TGGTACTGTT GGAACCACCT     120
AAATCACCAG TTCTGATACC TGCATCC                                         147
```

( 2 ) INFORMATION FOR SEQ ID NO:33:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i i ) IMMEDIATE SOURCE:
        ( B ) CLONE: oligonucleotide ( x i ) SEQUENCE DESCRIPTION: SEQ ID NO:33:

```
CTAGCGAGCT CAAGCTTA                                                    18
```

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: misc_binding
        ( B ) LOCATION: (6 7)
        ( D ) OTHER INFORMATION: /standard_name="site AccI"

( x i ) SEQUENCE DESCRIPTION: SEQ ID NO:34:

```
ATTACGTATA CAGAC                                                       15
```

( 2 ) INFORMATION FOR SEQ ID NO:35:

( i ) SEQUENCE CHARACTERISTICS:
        ( A ) LENGTH: 88 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:35:

```
CGATATACAC AATGCGTTTC TCTACTACAG TCGCTACTGC AGCTACTGCG CTATTTTCA       60
CAGCCTCCCC AAGTTTCAGC TATTACGT                                         88
```

( 2 ) INFORMATION FOR SEQ ID NO:36:

( i ) SEQUENCE CHARACTERISTICS:
 ( A ) LENGTH: 1121 base pairs
 ( B ) TYPE: nucleic acid
 ( C ) STRANDEDNESS: single
 ( D ) TOPOLOGY: linear ( i i ) MOLECULE TYPE: DNA (genomic)

( v i i ) IMMEDIATE SOURCE:
 ( B ) CLONE: 9C ( i x ) FEATURE:
 ( A ) NAME/KEY: misc_signal
 ( B ) LOCATION: 301
 ( D ) OTHER INFORMATION: /function="start of clone 9A"

( i x ) FEATURE:
 ( A ) NAME/KEY: misc_difference
 ( B ) LOCATION: replace(508, "")
 ( D ) OTHER INFORMATION: /standard_name="base is A in clone 9A"

( i x ) FEATURE:
 ( A ) NAME/KEY: misc_difference
 ( B ) LOCATION: replace(901, "")
 ( D ) OTHER INFORMATION: /standard_name="base is G in clone 9A"

( i x ) FEATURE:
 ( A ) NAME/KEY: CDS
 ( B ) LOCATION: 109..1017

( x i ) SEQUENCE DESCRIPTION: SEQ ID NO:36:

| | | | | | |
|---|---|---|---|---|---|
| AAACCCTCAC | TGCCTCTCTC | ATTCCTTCCG | GTGCCCCCGA | TCCTCAATCC | AACTTGTACA | 60 |
| TACTTCTCCC | AACTCTCTGC | TATATCCTTC | ATATTCCCAT | ACTACAAG ATG | TCC GCA | 117 |
| | | | | Met | Ser Ala |
| | | | | | 1 |

| GTA | AAA | GCA | GCC | CGC | TAC | GGC | AAG | GAC | AAT | GTC | CGC | GTC | TAC | AAG | GTT | 165 |
|---|---|---|---|---|---|---|---|---|---|---|---|---|---|---|---|---|
| Val | Lys | Ala | Ala | Arg | Tyr | Gly | Lys | Asp | Asn | Val | Arg | Val | Tyr | Lys | Val | |
| | 5 | | | | 10 | | | | | 15 | | | | | | |

| CAC | AAG | GAC | GAG | AAG | ACC | GGT | GTC | CAG | ACG | GTG | TAC | GAG | ATG | ACC | GTC | 213 |
|---|---|---|---|---|---|---|---|---|---|---|---|---|---|---|---|---|
| His | Lys | Asp | Glu | Lys | Thr | Gly | Val | Gln | Thr | Val | Tyr | Glu | Met | Thr | Val | |
| 20 | | | | | 25 | | | | 30 | | | | | | 35 | |

| TGT | GTG | CTT | CTG | GAG | GGT | GAG | ATT | GAG | ACC | TCT | TAC | ACC | AAG | GCC | GAC | 261 |
|---|---|---|---|---|---|---|---|---|---|---|---|---|---|---|---|---|
| Cys | Val | Leu | Leu | Glu | Gly | Glu | Ile | Glu | Thr | Ser | Tyr | Thr | Lys | Ala | Asp | |
| | | | | 40 | | | | | 45 | | | | | 50 | | |

| AAC | AGC | GTC | ATT | GTC | GCA | ACC | GAC | TCC | ATT | AAG | AAC | ACC | ATT | TAC | ATC | 309 |
|---|---|---|---|---|---|---|---|---|---|---|---|---|---|---|---|---|
| Asn | Ser | Val | Ile | Val | Ala | Thr | Asp | Ser | Ile | Lys | Asn | Thr | Ile | Tyr | Ile | |
| | | | 55 | | | | | 60 | | | | | 65 | | | |

| ACC | GCC | AAG | CAG | AAC | CCC | GTT | ACT | CCT | CCC | GAG | CTG | TTC | GGC | TCC | ATC | 357 |
|---|---|---|---|---|---|---|---|---|---|---|---|---|---|---|---|---|
| Thr | Ala | Lys | Gln | Asn | Pro | Val | Thr | Pro | Pro | Glu | Leu | Phe | Gly | Ser | Ile | |
| | | 70 | | | | | 75 | | | | | 80 | | | | |

| CTG | GGC | ACA | CAC | TTC | ATT | GAG | AAG | TAC | AAC | CAC | ATC | CAT | GCC | GCT | CAC | 405 |
|---|---|---|---|---|---|---|---|---|---|---|---|---|---|---|---|---|
| Leu | Gly | Thr | His | Phe | Ile | Glu | Lys | Tyr | Asn | His | Ile | His | Ala | Ala | His | |
| | 85 | | | | | 90 | | | | | 95 | | | | | |

| GTC | AAC | ATT | GTC | TGC | CAC | CGC | TGG | ACC | CGG | ATG | GAC | ATT | GAC | GGC | AAG | 453 |
|---|---|---|---|---|---|---|---|---|---|---|---|---|---|---|---|---|
| Val | Asn | Ile | Val | Cys | His | Arg | Trp | Thr | Arg | Met | Asp | Ile | Asp | Gly | Lys | |
| 100 | | | | | 105 | | | | | 110 | | | | | 115 | |

| CCA | CAC | CCT | CAC | TCC | TTC | ATC | CGC | GAC | AGC | GAG | GAG | AAG | CGG | AAT | GTG | 501 |
|---|---|---|---|---|---|---|---|---|---|---|---|---|---|---|---|---|
| Pro | His | Pro | His | Ser | Phe | Ile | Arg | Asp | Ser | Glu | Glu | Lys | Arg | Asn | Val | |
| | | | | 120 | | | | | 125 | | | | | 130 | | |

| CAG | GTG | GAC | GTG | GTC | GAG | GGC | AAG | GGC | ATC | GAT | ATC | AAG | TCG | TCT | CTG | 549 |
|---|---|---|---|---|---|---|---|---|---|---|---|---|---|---|---|---|
| Gln | Val | Asp | Val | Val | Glu | Gly | Lys | Gly | Ile | Asp | Ile | Lys | Ser | Ser | Leu | |
| | | | 135 | | | | | 140 | | | | | 145 | | | |

| TCC | GGC | CTG | ACC | GTG | CTG | AAG | AGC | ACC | AAC | TCG | CAG | TTC | TGG | GGC | TTC | 597 |
|---|---|---|---|---|---|---|---|---|---|---|---|---|---|---|---|---|
| Ser | Gly | Leu | Thr | Val | Leu | Lys | Ser | Thr | Asn | Ser | Gln | Phe | Trp | Gly | Phe | |
| | | 150 | | | | | 155 | | | | | 160 | | | | |

| CTG | CGT | GAC | GAG | TAC | ACC | ACA | CTT | AAG | GAG | ACC | TGG | GAC | CGT | ATC | CTG | 645 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Leu | Arg | Asp | Glu | Tyr | Thr | Thr | Leu | Lys | Glu | Thr | Trp | Asp | Arg | Ile | Leu | |
|     | 165 |     |     |     |     | 170 |     |     |     |     | 175 |     |     |     |     | |
| AGC | ACC | GAC | GTC | GAT | GCC | ACT | TGG | CAG | TGG | AAG | AAT | TTC | AGT | GGA | CTC | 693 |
| Ser | Thr | Asp | Val | Asp | Ala | Thr | Trp | Gln | Trp | Lys | Asn | Phe | Ser | Gly | Leu | |
| 180 |     |     |     |     | 185 |     |     |     |     | 190 |     |     |     |     | 195 | |
| CAG | GAG | GTC | CGC | TCG | CAC | GTG | CCT | AAG | TTC | GAT | GCT | ACC | TGG | GCC | ACT | 741 |
| Gln | Glu | Val | Arg | Ser | His | Val | Pro | Lys | Phe | Asp | Ala | Thr | Trp | Ala | Thr | |
|     |     |     |     | 200 |     |     |     |     | 205 |     |     |     |     | 210 |     | |
| GCT | CGC | GAG | GTC | ACT | CTG | AAG | ACT | TTT | GCT | GAA | GAT | AAC | AGT | GCC | AGC | 789 |
| Ala | Arg | Glu | Val | Thr | Leu | Lys | Thr | Phe | Ala | Glu | Asp | Asn | Ser | Ala | Ser | |
|     |     |     |     | 215 |     |     |     |     | 220 |     |     |     |     | 225 |     | |
| GTG | CAG | GCC | ACT | ATG | TAC | AAG | ATG | GCA | GAG | CAA | ATC | CTG | GCG | CGC | CAG | 837 |
| Val | Gln | Ala | Thr | Met | Tyr | Lys | Met | Ala | Glu | Gln | Ile | Leu | Ala | Arg | Gln | |
|     |     | 230 |     |     |     |     | 235 |     |     |     |     | 240 |     |     |     | |
| CAG | CTG | ATC | GAG | ACT | GTC | GAG | TAC | TCG | TTG | CCT | AAC | AAG | CAC | TAT | TTC | 885 |
| Gln | Leu | Ile | Glu | Thr | Val | Glu | Tyr | Ser | Leu | Pro | Asn | Lys | His | Tyr | Phe | |
|     | 245 |     |     |     |     | 250 |     |     |     |     | 255 |     |     |     |     | |
| GAA | ATC | GAC | CTG | AGC | TGG | CAC | AAG | GGC | CTC | CAA | AAC | ACC | GGC | AAG | AAC | 933 |
| Glu | Ile | Asp | Leu | Ser | Trp | His | Lys | Gly | Leu | Gln | Asn | Thr | Gly | Lys | Asn | |
| 260 |     |     |     |     | 265 |     |     |     |     | 270 |     |     |     |     | 275 | |
| GCC | GAG | GTC | TTC | GCT | CCT | CAG | TCG | GAC | CCC | AAC | GGT | CTG | ATC | AAG | TGT | 981 |
| Ala | Glu | Val | Phe | Ala | Pro | Gln | Ser | Asp | Pro | Asn | Gly | Leu | Ile | Lys | Cys | |
|     |     |     |     | 280 |     |     |     |     | 285 |     |     |     |     | 290 |     | |
| ACC | GTC | GGC | CGG | TCC | TCT | CTG | AAG | TCT | AAA | TTG | TAAACCAACA | TGATTCTCAC | | | | 1034 |
| Thr | Val | Gly | Arg | Ser | Ser | Leu | Lys | Ser | Lys | Leu | | | | | | |
|     |     |     | 295 |     |     |     |     | 300 |     |     | | | | | | |

GTTCCGGAGT TTCCAAGGCA AACTGTATAT AGTCTGGGAT AGGGTATAGC ATTCATTCAC   1094

TTGTTTTTTA CTTCCAAAAA AAAAAAA   1121

(2) INFORMATION FOR SEQ ID NO:37:

(i) SEQUENCE CHARACTERISTICS:
      (A) LENGTH: 302 amino acids
      (B) TYPE: amino acid
      (D) TOPOLOGY: linear (ii) MOLECULE TYPE: protein (xi) SEQUENCE DESCRIPTION: SEQ ID NO:37:

|     |     |     |     |     |     |     |     |     |     |     |     |     |     |     |
| --- | --- | --- | --- | --- | --- | --- | --- | --- | --- | --- | --- | --- | --- | --- |
| Met | Ser | Ala | Val | Lys | Ala | Ala | Arg | Tyr | Gly | Lys | Asp | Asn | Val | Arg | Val |
| 1   |     |     |     | 5   |     |     |     |     | 10  |     |     |     |     | 15  |     |
| Tyr | Lys | Val | His | Lys | Asp | Glu | Lys | Thr | Gly | Val | Gln | Thr | Val | Tyr | Glu |
|     |     |     | 20  |     |     |     |     | 25  |     |     |     |     | 30  |     |     |
| Met | Thr | Val | Cys | Val | Leu | Leu | Glu | Gly | Glu | Ile | Glu | Thr | Ser | Tyr | Thr |
|     |     | 35  |     |     |     |     | 40  |     |     |     |     | 45  |     |     |     |
| Lys | Ala | Asp | Asn | Ser | Val | Ile | Val | Ala | Thr | Asp | Ser | Ile | Lys | Asn | Thr |
|     | 50  |     |     |     |     | 55  |     |     |     |     | 60  |     |     |     |     |
| Ile | Tyr | Ile | Thr | Ala | Lys | Gln | Asn | Pro | Val | Thr | Pro | Pro | Glu | Leu | Phe |
| 65  |     |     |     |     | 70  |     |     |     |     | 75  |     |     |     |     | 80  |
| Gly | Ser | Ile | Leu | Gly | Thr | His | Phe | Ile | Glu | Lys | Tyr | Asn | His | Ile | His |
|     |     |     |     | 85  |     |     |     |     | 90  |     |     |     |     | 95  |     |
| Ala | Ala | His | Val | Asn | Ile | Val | Cys | His | Arg | Trp | Thr | Arg | Met | Asp | Ile |
|     |     |     | 100 |     |     |     |     | 105 |     |     |     |     | 110 |     |     |
| Asp | Gly | Lys | Pro | His | Pro | His | Ser | Phe | Ile | Arg | Asp | Ser | Glu | Glu | Lys |
|     |     | 115 |     |     |     |     | 120 |     |     |     |     | 125 |     |     |     |
| Arg | Asn | Val | Gln | Val | Asp | Val | Val | Glu | Gly | Lys | Gly | Ile | Asp | Ile | Lys |
|     | 130 |     |     |     |     | 135 |     |     |     |     | 140 |     |     |     |     |
| Ser | Ser | Leu | Ser | Gly | Leu | Thr | Val | Leu | Lys | Ser | Thr | Asn | Ser | Gln | Phe |
| 145 |     |     |     |     | 150 |     |     |     |     | 155 |     |     |     |     | 160 |
| Trp | Gly | Phe | Leu | Arg | Asp | Glu | Tyr | Thr | Thr | Leu | Lys | Glu | Thr | Trp | Asp |

```
                   165                        170                           175
Arg Ile Leu Ser Thr Asp Val Asp Ala Thr Trp Gln Trp Lys Asn Phe
            180                 185                 190

Ser Gly Leu Gln Glu Val Arg Ser His Val Pro Lys Phe Asp Ala Thr
        195                 200                 205

Trp Ala Thr Ala Arg Glu Val Thr Leu Lys Thr Phe Ala Glu Asp Asn
    210                 215                 220

Ser Ala Ser Val Gln Ala Thr Met Tyr Lys Met Ala Glu Gln Ile Leu
225                 230                 235                 240

Ala Arg Gln Gln Leu Ile Glu Thr Val Glu Tyr Ser Leu Pro Asn Lys
                245                 250                 255

His Tyr Phe Glu Ile Asp Leu Ser Trp His Lys Gly Leu Gln Asn Thr
            260                 265                 270

Gly Lys Asn Ala Glu Val Phe Ala Pro Gln Ser Asp Pro Asn Gly Leu
        275                 280                 285

Ile Lys Cys Thr Val Gly Arg Ser Ser Leu Lys Ser Lys Leu
        290                 295                 300
```